United States Patent
Chan et al.

(10) Patent No.: US 7,225,494 B2
(45) Date of Patent: Jun. 5, 2007

(54) MULTI-MOTION TOOTHBRUSH

(75) Inventors: John Geoffrey Chan, Loveland, OH (US); Wang Ping, Beijing (CN); Lawrence A. Blaustein, Moreland Hills, OH (US); Douglas A. Gall, Westlake, OH (US); Patrick W. Brown, Auburn, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 241 days.

(21) Appl. No.: 10/208,213

(22) Filed: Jul. 30, 2002

(65) Prior Publication Data

US 2003/0084528 A1 May 8, 2003

Related U.S. Application Data

(63) Continuation-in-part of application No. 10/027,594, filed on Dec. 21, 2001, now abandoned, which is a continuation-in-part of application No. 10/036,613, filed on Nov. 7, 2001, now abandoned, which is a continuation-in-part of application No. 09/993,167, filed on Nov. 6, 2001, now Pat. No. 6,725,490.

(51) Int. Cl.
A61C 17/34 (2006.01)

(52) U.S. Cl. .............................. 15/22.1; 15/22.2; 15/28

(58) Field of Classification Search ................. 15/22.1, 15/22.2, 22.4, 28, 29
See application file for complete search history.

(56) References Cited

U.S. PATENT DOCUMENTS

| 1,212,001 A | 1/1917 | Baxter ......................... 15/22.4 |
| 1,255,028 A | 1/1918 | Leonard et al. ................ 601/89 |
| 1,557,244 A | 10/1925 | Domingue |
| 1,945,616 A | 2/1934 | Mastrud |
| 2,044,863 A | 6/1936 | Sticht |
| 2,140,307 A * | 12/1938 | Belaschk et al. .............. 15/28 |
| 2,215,031 A | 9/1940 | Elmore .......................... 15/28 |
| 2,379,049 A | 6/1945 | Tompkins ................... 15/22.1 |
| 2,682,066 A | 6/1954 | Keely .......................... 15/22.1 |
| 2,799,878 A | 7/1957 | Brausch ...................... 15/22.1 |

(Continued)

FOREIGN PATENT DOCUMENTS

CA    1082408    7/1980

(Continued)

OTHER PUBLICATIONS

PUB Bader, Review of Currently Available Battery-Operated Toothbrushes, Compend. Conti. Educ. Dent., vol. XIII, No. 12, p. 1162, 1164-69.

(Continued)

*Primary Examiner*—Mark Spisich
(74) *Attorney, Agent, or Firm*—K. Bradford Adolphson

(57) ABSTRACT

An electric toothbrush is provided. The electric toothbrush includes a handle having a motor disposed therein, a head having a longitudinal axis, and a neck disposed between the handle and the head. First and second bristle holders are associated with the head. The first bristle holder oscillates or rotates. The second bristle holder is reciprocates in generally the same direction as the longitudinal axis of the head but does not rotate or oscillate. The motor is operatively connected to the first and second bristle holders.

20 Claims, 17 Drawing Sheets

U.S. PATENT DOCUMENTS

| | | | | |
|---|---|---|---|---|
| 3,103,027 A | 9/1963 | Birch | | 15/110 |
| 3,129,449 A | 4/1964 | Cyzer | | 15/28 |
| 3,142,852 A | 8/1964 | Phaneuf et al. | | |
| 3,160,902 A | 12/1964 | Aymar | | |
| 3,230,562 A | 1/1966 | Birch | | 15/110 |
| 3,242,516 A | 3/1966 | Cantor | | 15/28 |
| 3,284,829 A | 11/1966 | Allen | | 15/22.1 |
| 3,379,906 A | 4/1968 | Spohr | | |
| 3,577,579 A | 5/1971 | Duve | | 15/22.1 |
| 3,588,936 A | 6/1971 | Duve | | |
| 4,081,876 A | 4/1978 | Pugh | | |
| 4,131,967 A | 1/1979 | Northemann et al. | | 15/167.2 |
| 4,156,620 A | 5/1979 | Clemens | | 134/6 |
| 4,181,997 A | 1/1980 | O'Rourke | | 15/24 |
| 4,274,173 A | 6/1981 | Cohen | | 15/28 |
| 4,344,202 A | 8/1982 | Hayat | | |
| 4,365,376 A | 12/1982 | Oda et al. | | |
| 4,397,055 A | 8/1983 | Cuchiara | | |
| 4,420,851 A | 12/1983 | Wiener | | |
| 4,479,516 A | 10/1984 | Hunter | | 15/22.1 |
| 4,545,087 A | 10/1985 | Nahum | | 15/22.1 |
| 4,603,448 A | 8/1986 | Middleton et al. | | |
| 4,766,630 A | 8/1988 | Hegemann | | |
| 4,795,347 A | 1/1989 | Maurer | | |
| 4,827,550 A | 5/1989 | Graham et al. | | 15/22.1 |
| 4,845,795 A | 7/1989 | Crawford et al. | | |
| 4,894,880 A | 1/1990 | Aznavoorian | | |
| 4,989,287 A | 2/1991 | Scherer | | |
| 5,020,179 A | 6/1991 | Scherer | | |
| 5,033,150 A | 7/1991 | Gross et al. | | |
| 5,035,020 A | 7/1991 | Winiewski | | |
| 5,046,213 A | 9/1991 | Curtis et al. | | |
| D321,285 S | 11/1991 | Hirabayashi | | D4/101 |
| 5,068,939 A | 12/1991 | Holland | | 15/22.1 |
| 5,070,567 A | 12/1991 | Holland | | 15/28 |
| 5,077,855 A | 1/1992 | Ambasz | | 15/22.1 |
| 5,088,145 A | 2/1992 | Whitefield | | 15/22.1 |
| 5,099,536 A | 3/1992 | Hirabayashi | | 15/28 |
| 5,120,225 A | 6/1992 | Amit | | |
| 5,138,734 A | 8/1992 | Chung | | 15/28 |
| 5,142,723 A | 9/1992 | Lustig et al. | | 15/22.1 |
| 5,145,369 A | 9/1992 | Lustig et al. | | 433/118 |
| 5,148,567 A | 9/1992 | Daub | | |
| D330,286 S | 10/1992 | Curtis et al. | | |
| 5,170,525 A | 12/1992 | Cafaro | | |
| 5,177,826 A | 1/1993 | Vrignaud et al. | | |
| 5,186,627 A | 2/1993 | Amit et al. | | 433/216 |
| D334,473 S | 4/1993 | Volpenhein et al. | | D4/104 |
| 5,226,206 A | 7/1993 | Davidowitz et al. | | |
| 5,259,083 A | 11/1993 | Stansbury, Jr. | | |
| 5,274,870 A | 1/1994 | Stollman | | |
| 5,276,932 A | 1/1994 | Byrd | | 15/28 |
| 5,283,921 A | 2/1994 | Ng | | |
| 5,284,168 A | 2/1994 | Klinkhammer | | |
| 5,335,389 A | 8/1994 | Curtis et al. | | |
| 5,353,460 A | 10/1994 | Bauman | | 15/22.1 |
| 5,359,747 A | 11/1994 | Amakasu | | |
| 5,360,025 A | 11/1994 | Klinkhammer | | |
| 5,360,026 A | 11/1994 | Klinkhammer | | |
| 5,383,242 A | 1/1995 | Bigler et al. | | |
| 5,392,483 A | 2/1995 | Heinzelman et al. | | |
| 5,404,608 A | 4/1995 | Hommann | | |
| 5,416,942 A | 5/1995 | Baldacci et al. | | |
| 5,435,032 A | 7/1995 | McDougall | | 15/22.1 |
| 5,435,034 A | 7/1995 | Bigler et al. | | 15/22.1 |
| 5,442,827 A | 8/1995 | Hommann | | 15/22.1 |
| 5,446,940 A | 9/1995 | Curtis et al. | | |
| 5,448,792 A | 9/1995 | Wiedemann et al. | | |
| 5,465,444 A | 11/1995 | Bigler et al. | | |
| 5,493,747 A | 2/1996 | Inakagata et al. | | |
| 5,500,970 A | 3/1996 | Maurer et al. | | 15/22.1 |
| 5,504,958 A | 4/1996 | Herzog | | 15/22.1 |
| 5,504,959 A | 4/1996 | Yukawa | | |
| 5,504,960 A | 4/1996 | Hommann | | 15/22.1 |
| 5,507,959 A | 4/1996 | Glick | | 15/22.1 |
| 5,524,312 A * | 6/1996 | Tan et al. | | 15/22.1 |
| 5,617,601 A | 4/1997 | McDougall | | |
| 5,617,603 A * | 4/1997 | Mei | | 15/22.1 |
| 5,625,916 A | 5/1997 | McDougall | | |
| 5,628,082 A * | 5/1997 | Moskovich | | 15/110 |
| 5,679,991 A | 10/1997 | Wolf | | |
| 5,700,146 A | 12/1997 | Kucar | | |
| 5,715,556 A | 2/1998 | Chung | | 15/22.1 |
| 5,727,273 A | 3/1998 | Pai | | 15/22.1 |
| 5,732,432 A | 3/1998 | Hui | | |
| 5,732,433 A * | 3/1998 | Gocking et al. | | 15/28 |
| 5,735,011 A | 4/1998 | Asher | | 15/167.1 |
| 5,778,474 A | 7/1998 | Shek | | 15/22.1 |
| 5,784,743 A | 7/1998 | Shek | | 15/22.1 |
| D397,252 S | 8/1998 | Allende | | D4/101 |
| 5,802,656 A | 9/1998 | Dawson et al. | | 15/110 |
| 5,836,030 A | 11/1998 | Hazeu et al. | | |
| 5,842,244 A | 12/1998 | Hilfinger et al. | | 15/22.1 |
| 5,842,245 A * | 12/1998 | Pai | | 15/22.1 |
| 5,842,249 A | 12/1998 | Sato | | 15/167.2 |
| 5,850,603 A | 12/1998 | Lantto | | |
| 5,850,655 A | 12/1998 | Gocking et al. | | 15/28 |
| 5,867,856 A | 2/1999 | Herzog | | |
| 5,876,206 A | 3/1999 | Maurer | | |
| 5,894,620 A | 4/1999 | Polaert et al. | | |
| 5,901,397 A | 5/1999 | Hafele et al. | | |
| 5,974,613 A | 11/1999 | Herzog | | |
| 5,974,615 A | 11/1999 | Schwarz-Hartmann et al. | | |
| 5,996,157 A | 12/1999 | Smith et al. | | 15/28 |
| 6,000,083 A | 12/1999 | Blaustein et al. | | 15/28 |
| 6,006,394 A | 12/1999 | Bredall et al. | | |
| 6,032,313 A | 3/2000 | Tsang | | |
| 6,106,290 A | 8/2000 | Weissman | | 433/122 |
| D432,312 S | 10/2000 | Blaustein et al. | | D4/104 |
| 6,138,310 A | 10/2000 | Porper et al. | | |
| D433,814 S | 11/2000 | Blaustein et al. | | D4/104 |
| D434,563 S | 12/2000 | Lim et al. | | |
| 6,178,579 B1 | 1/2001 | Blaustein et al. | | |
| 6,189,693 B1 | 2/2001 | Blaustein et al. | | 206/362.2 |
| 6,195,828 B1 * | 3/2001 | Fritsch | | 15/22.1 |
| 6,209,164 B1 | 4/2001 | Sato | | 15/167.2 |
| 6,230,717 B1 | 5/2001 | Marx et al. | | |
| 6,237,178 B1 | 5/2001 | Krammer et al. | | 15/22.1 |
| 6,308,358 B2 | 10/2001 | Gruber et al. | | 15/22.1 |
| 6,308,359 B2 | 10/2001 | Fritsch et al. | | |
| 6,311,837 B1 | 11/2001 | Blaustein et al. | | 206/362.2 |
| 6,349,442 B1 | 2/2002 | Cohen et al. | | 15/22.1 |
| 6,371,294 B1 | 4/2002 | Blaustein et al. | | 206/362.2 |
| D456,998 S | 5/2002 | Blaustein et al. | | D4/101 |
| D457,728 S | 5/2002 | Blaustein et al. | | D4/104 |
| D458,030 S | 6/2002 | Blaustein et al. | | D4/104 |
| D458,455 S | 6/2002 | Blaustein et al. | | D4/104 |
| D459,894 S | 7/2002 | Blaustein et al. | | D4/107 |
| D459,895 S | 7/2002 | Blaustein et al. | | D4/107 |
| 6,421,865 B1 | 7/2002 | McDougall | | 15/22.1 |
| 6,421,866 B1 | 7/2002 | McDougall | | 15/22.1 |
| 6,421,867 B1 | 7/2002 | Weihrauch | | |
| D461,642 S | 8/2002 | Blaustein et al. | | D4/107 |
| 6,434,773 B1 | 8/2002 | Kuo | | 15/22.1 |
| D465,088 S | 11/2002 | Blaustein et al. | | D4/101 |
| 6,574,820 B1 | 6/2003 | DePuydt et al. | | 15/28 |
| 6,630,395 B1 | 10/2003 | Kane | | |
| 6,725,490 B2 | 4/2004 | Blaustein et al. | | |
| 6,836,917 B2 | 1/2005 | Blaustein et al. | | 15/22.1 |
| 6,892,413 B2 | 5/2005 | Blaustein et al. | | |
| 2001/0001334 A1 | 5/2001 | Gruber et al. | | 15/22.1 |
| 2001/0004781 A1 | 6/2001 | Blaustein et al. | | 15/28 |
| 2001/0020314 A1 | 9/2001 | Calabrese | | 15/22.1 |
| 2001/0022277 A1 | 9/2001 | Blaustein et al. | | 206/362.2 |

| | | | | | | |
|---|---|---|---|---|---|---|
| 2001/0054561 A1 | 12/2001 | Blaustein et al. ........ 206/362.2 | GB | 2005999 A | | 5/1979 |
| 2002/0017474 A1 | 2/2002 | Blaustein et al. ........ 206/362.2 | GB | 1583558 | | 1/1981 |
| 2002/0020645 A1 | 2/2002 | Blaustein et al. ........ 206/362.2 | GB | 2228861 | | 9/1990 |
| 2002/0029988 A1 | 3/2002 | Blaustein et al. ........ 206/362.2 | GB | 2237505 | | 5/1991 |
| 2002/0032941 A1 | 3/2002 | Blaustein et al. ............ 15/22.1 | GB | 2247297 | * | 2/1992 |
| 2002/0038772 A1 | 4/2002 | Blaustein et al. ........ 206/362.2 | GB | 2290224 | | 12/1995 |
| 2002/0078514 A1 | 6/2002 | Blaustein et al. ............ 15/22.1 | GB | 2319170 | | 5/1998 |
| 2002/0129454 A1 | 9/2002 | Hilscher et al. | GB | 3004958 | | 7/2002 |
| 2002/0152564 A1 | 10/2002 | Blaustein et al. ............ 15/22.1 | JP | 301895 | | 6/1905 |
| 2002/0162180 A1 | 11/2002 | Blaustein et al. ............ 15/22.1 | JP | 57-89810 | | 6/1982 |
| 2003/0066145 A1 | 4/2003 | Prineppi .................... 15/22.1 | JP | 63-168108 | | 7/1988 |
| 2003/0084525 A1 | 5/2003 | Blaustein et al. | JP | 2-19241 | | 2/1990 |
| 2003/0084526 A1 | 5/2003 | Brown et al. | JP | 4-133733 | | 7/1991 |
| 2003/0084527 A1 | 5/2003 | Brown et al. | JP | 05-095816 | | 4/1993 |
| 2003/0226223 A1 | 12/2003 | Chan | JP | 5-146313 | * | 6/1993 |
| 2004/0083566 A1 | 5/2004 | Blaustein et al. | JP | 05-146314 | | 6/1993 |
| 2005/0000045 A1 | 1/2005 | Blaustein et al. | JP | 5-161509 | | 6/1993 |
| 2005/0005375 A1 | 1/2005 | Blaustein et al. | JP | 05-199917 | | 8/1993 |
| 2005/0005376 A1 | 1/2005 | Blaustein et al. | JP | 05 199918 | | 8/1993 |
| 2005/0022323 A1 | 2/2005 | Chan | JP | 05-269023 | | 10/1993 |
| | | | JP | 05-269024 | | 10/1993 |
| | FOREIGN PATENT DOCUMENTS | | JP | 6-047298 | | 2/1994 |
| | | | JP | 6-189822 | | 7/1994 |
| CA | 1330383 | 6/1994 | JP | 7-116023 | | 5/1995 |
| CA | 2141569 | 2/2000 | JP | 07-116024 | | 5/1995 |
| CN | 1105173 | 7/1995 | JP | 07-166020 | | 5/1995 |
| CN | 2236827 | 10/1996 | JP | 07-148020 | | 6/1995 |
| CN | 2271352 | 12/1997 | JP | 7-116024 | | 7/1995 |
| CN | 2271353 | 12/1997 | JP | 08-000356 | | 1/1996 |
| CN | 2274947 | 2/1998 | JP | 2511226 | | 7/1996 |
| CN | 330411 * | 4/1998 | JP | 08-299372 A | | 11/1996 |
| CN | 1187341 A | 7/1998 | JP | 507030 | | 7/1997 |
| CN | 97325183.2 | 12/1998 | JP | 2719556 | | 2/1998 |
| CN | 2324988 | 6/1999 | JP | 10-66704 | * | 3/1998 |
| DE | 1174293 | 7/1964 | JP | 10-507375 | | 7/1998 |
| DE | 1244709 | 1/1968 | JP | 2811246 | | 8/1998 |
| DE | 1457372 | 4/1969 | JP | 38-99036 U | | 7/2000 |
| DE | 2654853 | 6/1978 | JP | 3069418 | | 7/2000 |
| DE | 2736286 | 7/1978 | KR | 1984-0004668 | | 9/1984 |
| DE | 8426426.8 | 3/1985 | KR | 1986-0001137 | | 6/1986 |
| DE | 3406112 | 8/1985 | KR | 1991-700015 | | 3/1991 |
| DE | 4441571 | 12/1995 | KR | 1995-002814 | | 2/1995 |
| DE | 29600236 | 4/1996 | KR | 1995-0010820 | | 5/1995 |
| DE | 29600255 | 5/1996 | KR | 1997-000408 | | 1/1997 |
| DE | 29613608 | 11/1996 | KR | 1997-000409 | | 1/1997 |
| DE | 29618755 * | 3/1997 | KR | 143460 | | 4/1998 |
| DE | 29517610 | 4/1997 | KR | 1999-0028614 | | 3/2000 |
| DE | 29701302 | 8/1997 | KR | 183429 | | 3/2000 |
| DE | 29809977 U1 | 4/1999 | TW | 257968 | | 6/1905 |
| DE | 29821121 U1 | 4/1999 | TW | 96609 | | 6/1976 |
| DE | 19803311 | 8/1999 | TW | 154730 | | 3/1979 |
| EP | 0098275 | 11/1985 | TW | 164493 | | 7/1979 |
| EP | 254397 | 1/1988 | TW | 026360 | | 9/1979 |
| EP | 0259648 | 3/1988 | TW | 200663 | | 5/1981 |
| EP | 0374152 | 8/1988 | TW | 229411 | | 5/1982 |
| EP | 208401 | 5/1991 | TW | 248031 | | 12/1982 |
| EP | 520985 | 1/1993 | TW | 228087 | | 11/1983 |
| EP | 0537465 | 4/1993 | TW | 274724 | | 4/1984 |
| EP | 546203 | 6/1993 | TW | 135303 | | 6/1990 |
| EP | 0569606 | 11/1993 | TW | 137856 | | 7/1990 |
| EP | 0689404 | 1/1996 | TW | 238504 | | 6/1993 |
| EP | 758857 | 2/1997 | TW | 212909 | | 9/1993 |
| EP | 1053721 | 11/2000 | TW | 239963 | | 2/1995 |
| FR | 1121618 | 8/1956 | TW | 239964 | | 2/1995 |
| FR | 1166163 | 4/1958 | TW | 253174 | | 8/1995 |
| FR | 1525112 | 5/1968 | TW | 281884 | | 7/1996 |
| FR | 2337524 | 8/1977 | TW | 311444 | | 12/1996 |
| FR | 2368854 A | 6/1978 | TW | 309753 | | 7/1997 |
| GB | 452961 | 9/1936 | TW | 330410 | | 4/1998 |
| GB | 914844 | 1/1963 | TW | 330411 | | 4/1998 |
| GB | 989953 | 4/1965 | TW | 406557 | | 5/1998 |
| GB | 1008530 | 10/1965 | TW | 334345 | | 6/1998 |
| GB | 1240438 | 7/1971 | TW | 339233 | | 8/1998 |

| | | |
|---|---|---|
| TW | 455298 | 9/2001 |
| TW | 455299 | 9/2001 |
| WO | 83/03956 | 11/1983 |
| WO | 91/13570 | 9/1991 |
| WO | WO 92/13499 A1 | 8/1992 |
| WO | 92/19177 | 11/1992 |
| WO | 93/20777 | 10/1993 |
| WO | WO 94/03125 | 2/1994 |
| WO | 94/09676 | 5/1994 |
| WO | 94/21191 | 9/1994 |
| WO | 95/11636 | 5/1995 |
| WO | 95/27419 | 10/1995 |
| WO | 97/20484 | 6/1997 |
| WO | 97/25899 | 7/1997 |
| WO | WO 97/28757 A1 | 8/1997 |
| WO | 97/34545 | 9/1997 |
| WO | 98/26729 | 6/1998 |
| WO | 98/26730 | 6/1998 |
| WO | WO 98/23223 A1 | 6/1998 |
| WO | 99/12492 | 3/1999 |
| WO | WO 99/23910 A1 | 5/1999 |
| WO | 99/37180 | 7/1999 |
| WO | 99/56660 | 11/1999 |
| WO | 00/56186 | 9/2000 |
| WO | 00/78244 | 12/2000 |
| WO | WO 00/74522 A1 | 12/2000 |
| WO | WO 00/74592 A1 | 12/2000 |
| WO | 01/32095 | 5/2001 |
| WO | 01/52696 | 7/2001 |

OTHER PUBLICATIONS

Photographs of electric toothbrush of BioBrush Industries (22 photographs).

English Translation of Taiwan Patent Document TW 135303, Jun. 1990.

* cited by examiner

MULTI-MOTION TOOTHBRUSH

This is a continuation-in-part of U.S. application Ser. No. 10/027,594 filed Dec. 21, 2001 now abandoned, which is a continuation-in-part of U.S. application Ser. No. 09/993,167, filed Nov. 6, 2001 now U.S. Pat. No. 6,725,490, and the U.S. application Ser. No. 10/036,613, filed Nov. 7, 2001 now abandoned, the substances of which are incorporated herein by reference.

FIELD OF THE INVENTION

The invention relates to the field of toothbrushes, and more particularly, the invention relates to field of electrically powered toothbrushes.

BACKGROUND OF THE INVENTION

The art is replete with techniques for transforming the rotational output of a motor or other electromotive power source into desired brushing motions. Many techniques include a shaft as component of the drive train. The shaft may rotate, oscillate, or reciprocate. The shaft is coupled to a bristle holder. Most often, the bristle holder is driven by the shaft in a rotating or oscillating manner about an axis which is normal to the longitudinal axis of the shaft.

These electric toothbrushes typically provide only a single brushing motion. While single brushing motions are beneficial, it believed that multi-motion electric toothbrushes can provide superior cleaning action. Further, there is a desire to combine the cleaning action provided by the bristles of a rotating or oscillating bristle holder with the cleaning action of bristles that only reciprocate along a longitudinal axis of the electric toothbrush so as to more closely replicate a manual tooth brushing motion.

BRIEF SUMMARY OF THE INVENTION

An electric toothbrush is provided. The electric toothbrush includes a handle having a motor disposed therein, a head having a longitudinal axis, and a neck disposed between the handle and the head. First and second bristle holders are associated with the head. The first bristle holder oscillates or rotates. The second bristle holder is reciprocates in generally the same direction as the longitudinal axis of the head but does not rotate or oscillate. The motor is operatively connected to the first and second bristle holders.

BRIEF DESCRIPTION OF THE DRAWINGS

It is believed that the present invention will be better understood from the following description taken in conjunction with the accompanying drawings in which.

DETAILED DESCRIPTION OF THE INVENTION

Reference will now be made in detail to various embodiments of the present invention, examples of which are illustrated in the accompanying drawings wherein like numerals indicate the same elements throughout the views and wherein numerals having the same last two digits (e.g., 20 and 120) connote similar or corresponding elements. As will be appreciated, the present invention is directed to electric toothbrushes (including electric toothbrushes having replaceable heads) and electric toothbrush heads having first and second moving bristle holders. The first bristle holder rotates or oscillates while the second bristle holder reciprocates in the longitudinal direction of the head. In a more preferred form, the first bristle holder rotates or oscillates but does not reciprocate, translate, or perform any other non-rotational or oscillatory motion, and the second bristle holder reciprocates but does not rotate or oscillate. As used herein, the term "rotate" is intended to refer to a unidirectional angular motion (e.g., a constant clockwise motion) while the term "oscillate" is intended to refer to vibratory angular motion (e.g., repeated cycles of clockwise rotation and counter clockwise rotation). Vibration is any periodic movement having repeated cycles. Vibratory motion can have one or more frequencies and amplitudes. Vibratory motion that is substantially linear is referred to herein as a reciprocating motion.

The present invention can be used in combination with electric toothbrushes and electric toothbrush heads that include shafts that rotate, oscillate, or reciprocate (as well as combinations thereof) to impart motion to the first and second bristle holders. In addition, the present invention can be used in combination with electric toothbrushes and electric toothbrush heads where the shaft is operatively connected to both the first and second bristle holders or only one of the bristle holders. In the latter instance, the bristle holders are themselves interconnected so that a motion is imparted to the bristle holder that is not directly coupled to the shaft.

Referring to FIGS. 1 to 9, some exemplary electric toothbrushes made in accordance with the present invention will now be described. These electric toothbrushes utilize a shaft that rotates. While these embodiments will be described with respect to the particular motor and shaft arrangement illustrated in FIG. 1 for purposes of simplicity and clarity, it will be appreciated that other motor and rotating (or oscillating) shaft arrangements can be substituted. For example, U.S. Pat. Nos. 5,617,603; 5,850,603; 5,974,615; 6,032,313; 5,732,432; 5,070,567; 5,170,525; 5,416,942; 3,588,936; 5,867,856; and 4,397,055, the substances of which are incorporated herein by reference, disclose other motor and rotating or oscillating shaft arrangements that might be suitable.

Figure 1:
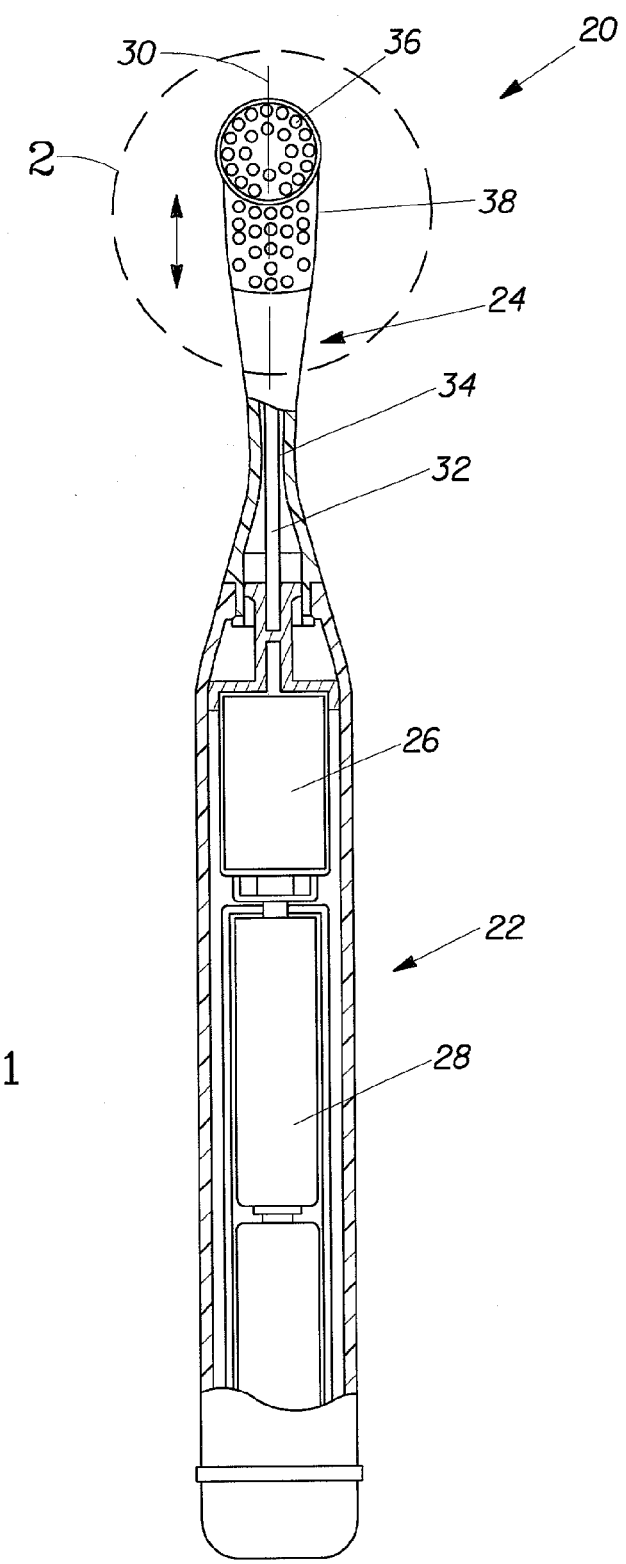
FIG. 1 is a planar, partial sectional, top view of an electric toothbrush made in accordance with the present invention, wherein the electric toothbrush incorporates a rotating or shaft.

Turning to FIG. 1, the electric toothbrush comprises a toothbrush head 20, a body or handle 22, and an elongated neck 24 there between. As used herein, the term "forward" is intended to refer to the direction from the handle to the head while the term "rearward" is intended to refer to the direction from the head to the handle. In addition, the term "longitudinal" is intended to refer to a lengthwise feature of an element as seen from a top planar view thereof. For example, a longitudinal axis is an axis passing through the longest dimension of an element, such as the head or a shaft. A longitudinal direction is a direction that generally corresponds to a longitudinal axis but which may not line in the same plane as the longitudinal axis. For example, the longitudinal axes of a shaft and a toothbrush head may not line in the same plane but generally extend in the same direction from a top planar view. Similarly, a neck and head that are angled with respect to each other may not have longitudinal axes which lie in the same plane, but do have axes which extend in the same general longitudinal direction from a top planar view. The electric toothbrushes of the present invention typically have an elongate head with a longitudinal axis passing through the longest dimension thereof. This axis typically extends in the same general direction as the longitudinal axes of the toothbrush neck and/or shaft. By the phrase "same general direction", some angular deviation is contemplated between the axes. The second bristle holder of these toothbrushes reciprocates in the same general direction as one or more of these axes. More preferably, the second bristle holder of these toothbrushes reciprocates in substantially the same or the same direction as one or more of these axes, although hereafter for simplicity only reciprocation in the same general direction is discussed.

The handle is hollow and includes a motor 26 and batteries 28 for powering the motor. A rechargeable power source can be substituted for the batteries. The head 20 has a longitudinal axis 30 passing there through. The longitudinal axis 30 extends in the same general longitudinal direction as a longitudinal axis 32 of a shaft 34. The shaft 34 is housed at least partially within neck 24. A first bristle holder 36 is disposed at a first end of the head 20, wherein the first end is at the forward most point of the head 20. While the first bristle holder 36 is illustrated as circular in shape, other shapes can be utilized. Further, while the first bristle holder 36 is disposed at the first end of the head 20, it will be appreciated that it can be disposed away from the first end and other features, such as stationary bristles, might be disposed between the first bristle holder 36 and the first end of the head 20. The first bristle holder 36 includes at least one slot for receiving a remote most end of the rotating shaft 34, as described in U.S. Pat. No. 5,625,916, the substance of which is incorporated herein by reference. The remote-most end of the shaft 34 is bent or offset from the longitudinal axis 32 of the shaft 34 and engages the slot to oscillate the first bristle holder 36 about a pin (not shown). In other words, the first bristle holder 36 oscillates about an axis approximately normal to the longitudinal axis 30, 32 of the head 20 and/or the shaft 34. In this embodiment, the first bristle holder only oscillates and does not reciprocate, translate, or perform any other non-rotational motion.

A second bristle holder 38 is disposed adjacent the first bristle holder 36. The second bristle holder 38 reciprocates in the same general longitudinal direction as longitudinal axis 30 of the head 20. In this embodiment, the longitudinal direction of reciprocation is also the same as the longitudinal direction of the longitudinal axis 32 of the shaft 34. While it is desirable to locate the second bristle holder 38 directly adjacent the first bristle holder 36, it is contemplated that a gap may be provided between the first and second bristle holders. In addition, the gap between the first and second bristle holders might be filled with stationary bristles which are embedded in fixed or stationary third bristle holder (not shown) which forms part of the toothbrush head. Further, while the first bristle holder 36 has been described as adjacent the first end of the head 20, it is contemplated that the second bristle holder 38 might be disposed adjacent the first end of the head 20 and driven in the same manner as described below with respect to FIG. 2.

In addition, the electric toothbrush of FIG. 1 might be provided with a replaceable head. A suitable arrangement that can be adapted to the present invention is disclosed in U.S. Pat. No. 5,617,601, the substance of which is incorporated herein by reference.

Figure 2:
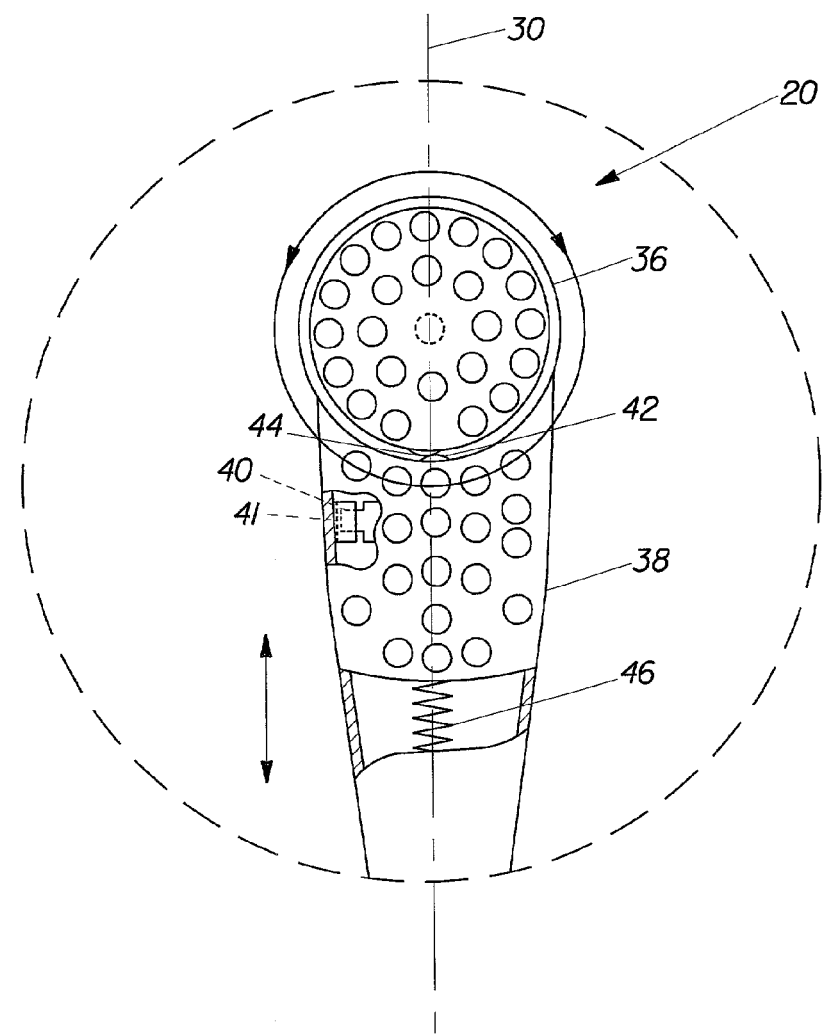
FIG. 2 is a planar, partial section top view of a first embodiment of a toothbrush head suitable for use with the electric toothbrush of FIG. 1.

Referring to FIG. 2, a first embodiment of a toothbrush head suitable for use the electric toothbrush of FIG. 1 will now be described in more detail. The second bristle holder 38 has a pair of opposed projections 40, one of which is illustrated, which are slideably received by slots 41, one of which is illustrated, of the head 20 to guide the second bristle holder 38 in its longitudinal motion. The slots are aligned in generally the same longitudinal direction as the longitudinal axis of the head 20. The second bristle holder 38 is driven in a reciprocating longitudinal motion by the movement of the first bristle holder 36 through a pair of opposed hemispherical protrusions 42, 44 that engage one another to displace the second bristle holder 38 against a biasing element, such as spring 46. As the protrusions cyclically engage and disengage each other as the first bristle holder 36 oscillates, the second bristle holder 38 is moved away from and then back toward the first bristle holder 36 with the cooperation of the spring 46. The protrusions are rigidly mounted to or integrally formed with the first and second bristle holders. As the motor 26 of the electric toothbrush rotates the shaft 34, the remote end of the shaft engages the slot of the first bristle holder 36 to oscillate the first bristle holder. As the first bristle holder 36 oscillates, the protrusion 44 disposed on the first bristle holder 36 comes into contact with the surface of the protrusion 42 on the second bristle holder 38, thereby displacing the second bristle holder 38 away from the first bristle holder in the same longitudinal direction as the longitudinal axis of the head 20. As the shaft 34 continues to rotate, the protrusion 44 of the first bristle holder 36 disengages from the other protrusion 42 so that the spring 46 can urge the second bristle holder 38 back toward the first bristle holder 36, thus completing one cycle. As the first bristle holder 36 reverses its direction of rotation, this cycle is repeated.

Figure 3:
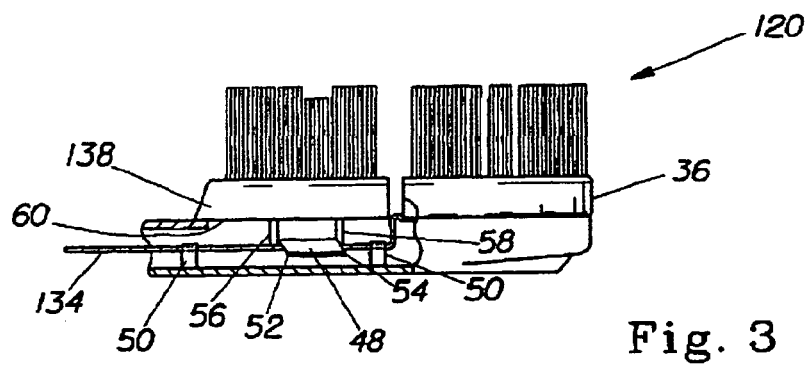
FIG. 3 is an elevational, partial sectional side view of a second embodiment of a toothbrush head suitable for use with the electric toothbrush of FIG. 1.

Referring to FIG. 3, a second embodiment of a toothbrush head suitable for use with the electric toothbrush of FIG. 1 will now be described. The head 120 also includes a second bristle holder 138 that is slideably mounted in slots (not shown, but which can be the same arrangement as the projection 40 and slot 41 arrangement illustrated in FIG. 2). The second bristle holder 138 is reciprocatingly driven in the same general longitudinal direction as the longitudinal axis of the head 20 and/or shaft 134. A cam 48 included on the shaft 134 operatively interconnects the shaft 134 with second bristle holder 138. Optionally, the shaft 134 can be supported by shaft supports 50. The shaft supports 50 may include C or U shaped portions (not shown) that receive the shaft 34. Other means for retaining the shaft 134 in a support are known in the art. The cam 48 can comprise a shaped element or bead, with an appropriate eccentric configuration, placed or molded over and firmly secured to the shaft 134. In one arrangement, the cam 48 is cylindrically shaped with a pair of acutely angled surfaces 52, 54 which are inclined in the same direction and at the same angle of inclination, but which are disposed at opposite ends of the cam 48. In other words, the angled surfaces 52, 54 are merely the surface resulting from a diagonal slice through the cylinder of the cam 48. The direction of inclination and angle of inclination can be varied as desired to change the frequency and stroke of the second bristle holder 138. First and second cam followers 56, 58 depend from a bottom surface 60 of the second bristle holder 138. The cam followers 56, 58 are offset or spaced from each other so that cam 48 is disposed between the cam followers 56, 58 which straddle and/or capture the cam 48. The angled surfaces 52, 54 of the cam 48 slidingly engage the free ends of the cam followers 56, 58. As the shaft 134 rotates, the first acutely angled surface 52 of the cam 48 comes into contact with a surface of the first cam follower 56 and drives the cam follower, and therefore, the second bristle holder 138, away from the first bristle holder 36 in a direction generally the same as the direction of the longitudinal axis of the head 120. The second bristle holder 138 is guided by the longitudinally extending slots. As the shaft 134 continues to rotate, the cam 48 disengages from the first cam follower 56. The second acutely angled second surface 54 of the cam 48 then comes into contact with a surface of the second cam follower 58 and drives the second cam follower 58, and therefore the second bristle holder 138, back toward the first bristle holder 36.

Figure 4:
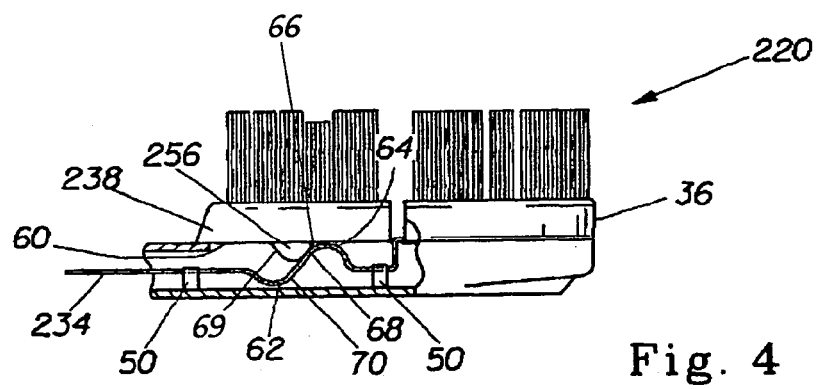
FIG. 4 is an elevational, partial sectional side view of a third embodiment of a toothbrush head suitable for use with the electric toothbrush of FIG. 1, wherein the second bristle holder is shown in a first position.
Figure 5:
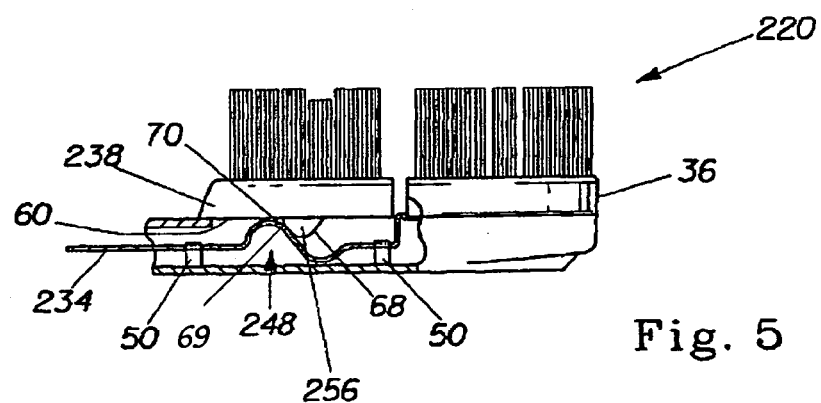
FIG. 5 is an elevational, partial sectional side view of the toothbrush head of FIG. 4, wherein the second bristle holder is shown in a second position.

Referring to FIGS. 4 and 5, a third embodiment of a toothbrush head suitable for use with the electric toothbrush of FIG. 1 will now be described. The head 220 includes a second bristle holder 238 that is slideably mounted in slots (not shown, but the same arrangement as the projection 40 and slot 41 arrangement illustrated in FIG. 2). The second bristle holder 238 is reciprocatingly driven in the same general longitudinal direction as the longitudinal axis of the head 220 and/or shaft 234. A cam 248 included on the shaft 234 operatively interconnects the shaft 234 with second bristle holder 238. Optionally, the shaft 234 can be supported by shaft supports 50. The shaft supports 50 may include C or U shaped portions (not shown) that receive the shaft 234. Other means for retaining the shaft 234 in a support are known in the art. The cam 248 is provided in the form of a plurality of bends 62, 64 in the shaft 234. The bends are sinusoidal or curvilinear in nature in that each bend has one or more adjacent arcuate portions. The bends each have an apex and the apexes are disposed on opposite sides of the shaft 234. A hemispherically-shaped cam follower 256 depends from a bottom surface 60 of the second bristle holder 238 and is disposed between the apexes of the cam 248. As the shaft 234 rotates, a first surface 66 of the cam 248 comes into contact with a first surface 68 of the cam follower 256 and drives the cam follower 256, and therefore the second bristle holder 238, away from the first bristle holder 36 in a longitudinal direction generally the same as the longitudinal axis of the head 220. As the shaft 234 continues to rotate, the forward most apex passes the cam 248 and disengages from the first cam follower surface 68. As shown in FIG. 5, a second surface 70 of the cam 248 then comes into contact with a second surface 69 of the cam follower 256 and drives the cam follower 256, and therefore the second bristle holder 238, back toward the first bristle holder 36. The stroke and frequency of the reciprocating motion of the second bristle holder 238 can be varied by changing the spacing between the apexes and/or the amplitude, shape, or height of the apexes.

Figure 6:
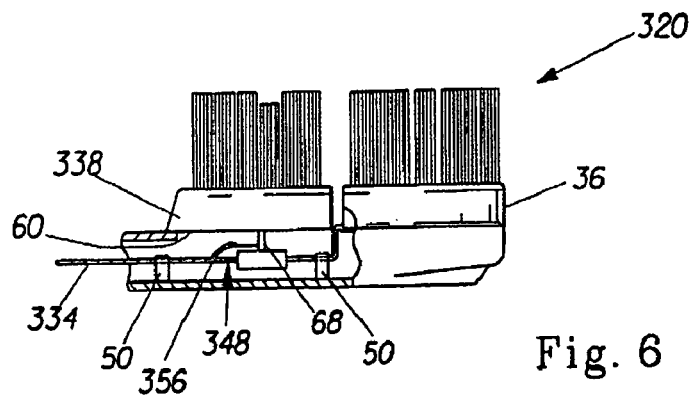
FIG. 6 is an elevational, partial sectional side view of a fourth embodiment of a toothbrush head suitable for use with the electric toothbrush of FIG. 1.
Figure 7:
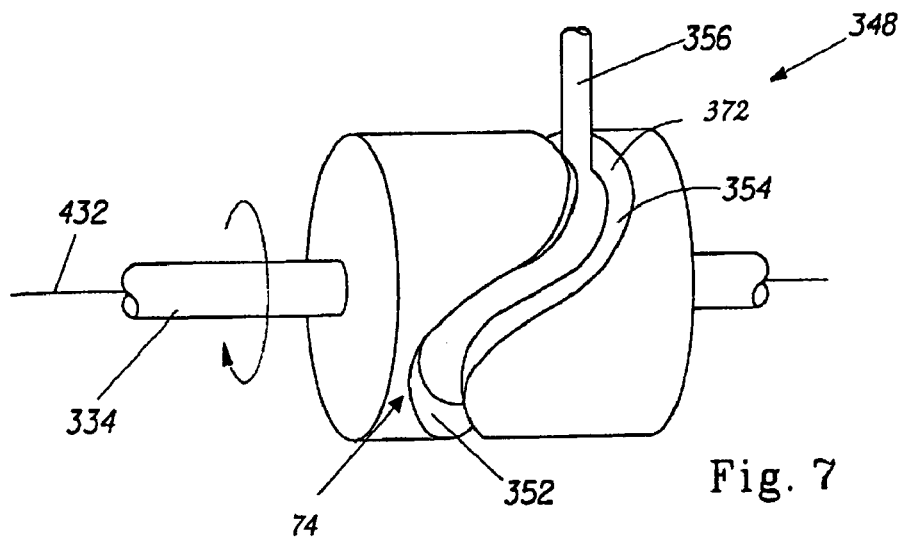
FIG. 7 is a perspective view of a cam suitable for use with the toothbrush head shown in FIG. 6.
Figure 8:
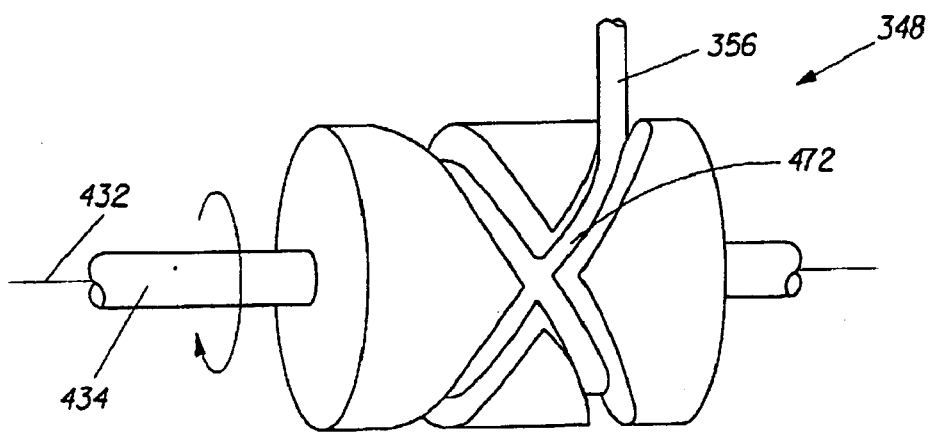
FIG. 8 is a perspective view of another cam suitable for use with the toothbrush head shown in FIG. 6.

Referring to FIG. 6, a fourth embodiment of a toothbrush head suitable for use with the electric toothbrush of FIG. 1 will now be described. The head 320 includes a second bristle holder 338 that is slideably mounted in slots (not shown, but which can be the same arrangement as the projection 40 and slot 41 arrangement illustrated in FIG. 2). The second bristle holder 338 is reciprocatingly driven in the same general longitudinal direction as the longitudinal axis of the head 320 and/or shaft 334. A cam 348 included on the shaft 334 operatively interconnects the shaft 334 with second bristle holder 338. Optionally, the shaft 334 can be supported by shaft supports 50. The shaft supports 50 may include C or U shaped portions (not shown) that receive the shaft 334. Other means for retaining the shaft 334 in a support are known in the art. The cam 348 is provided in the form of a cylindrically-shaped bead placed or molded over and firmly secured to the shaft 334. As shown in FIGS. 7 and 8, the cam 348 includes a spiral or helical groove 372 or 472, respectively. The spiral or helical groove 372 or 472 extends around the circumference of the bead and spirals about a longitudinal axis of the bead which may, for example, coincide with the longitudinal axis 432 of the shaft 334. The stroke and frequency of the motion imparted to the cam follower 356 by the cam 348 can be varied by changing the shape and dimensions of the groove. For example, the spiral groove 372 of cam 348 is sinusoidal in shape and would provide one complete stroke of the second bristle holder 338 (i.e., one cycle away from and back toward the first bristle holder 36) for one revolution of the shaft 334. FIG. 8 illustrates an alternate cam 348 having a helical groove 472 which is provided in the form of figure eight. This would only provide one-half of a stroke (i.e., only either translation toward or away from the first bristle holder 36) for one revolution of the shaft 334. A cam follower 356 depends from a bottom surface 60 of the second bristle holder 338. The cam follower 356 is slideably received within the groove 372. As the shaft 334 rotates, a first surface 354 of the spiral groove 372, such as a side wall thereof, comes into contact with a first surface of the cam follower 356 and drives the cam follower 356, and therefore the second bristle holder 338, away from the first bristle holder 36 in a longitudinal direction generally the same as the longitudinal axis of the head 320. As the shaft 334 continues to rotate, the cam follower 356 reaches an apex 74 of the spiral groove 372 and the first surface 354 of the spiral groove 372 disengages from the first surface 354 of the groove 372. A second surface 352 of the groove 372, such as the opposite side wall of the groove 372 then comes into contact with a second surface of the cam follower 356 and drives the cam follower 356, and therefore the second bristle holder 338, back toward the first bristle holder 36.

Referring to FIGS. 9 to 13, more exemplary electric toothbrushes made in accordance with the present invention will now be described. These electric toothbrushes utilize a shaft that reciprocates. While these embodiments will be described with respect to the particular motor and shaft arrangement illustrated in FIG. 9 for purposes of simplicity and clarity, it will be appreciated that other motor and reciprocating shaft arrangements can be substituted. For example, U.S. Pat. Nos. 5,226,206; 5,524,312; 5,383,242; 5,465,444; 5,504,959; 5,836,030; 4,845,795; 5,404,608; 5,359,747; and 5,617,601, the substances of which are incorporated herein by reference, disclose other motor and reciprocating shaft arrangements that might be suitable. In addition, the electric toothbrush of FIG. 9 might be provided with a replaceable head. A suitable arrangement which can be adapted to the present invention is disclosed in U.S. application Ser. No. 09/850,662, filed May 7, 2001, the substance of which is incorporated herein by reference.

Figure 9:
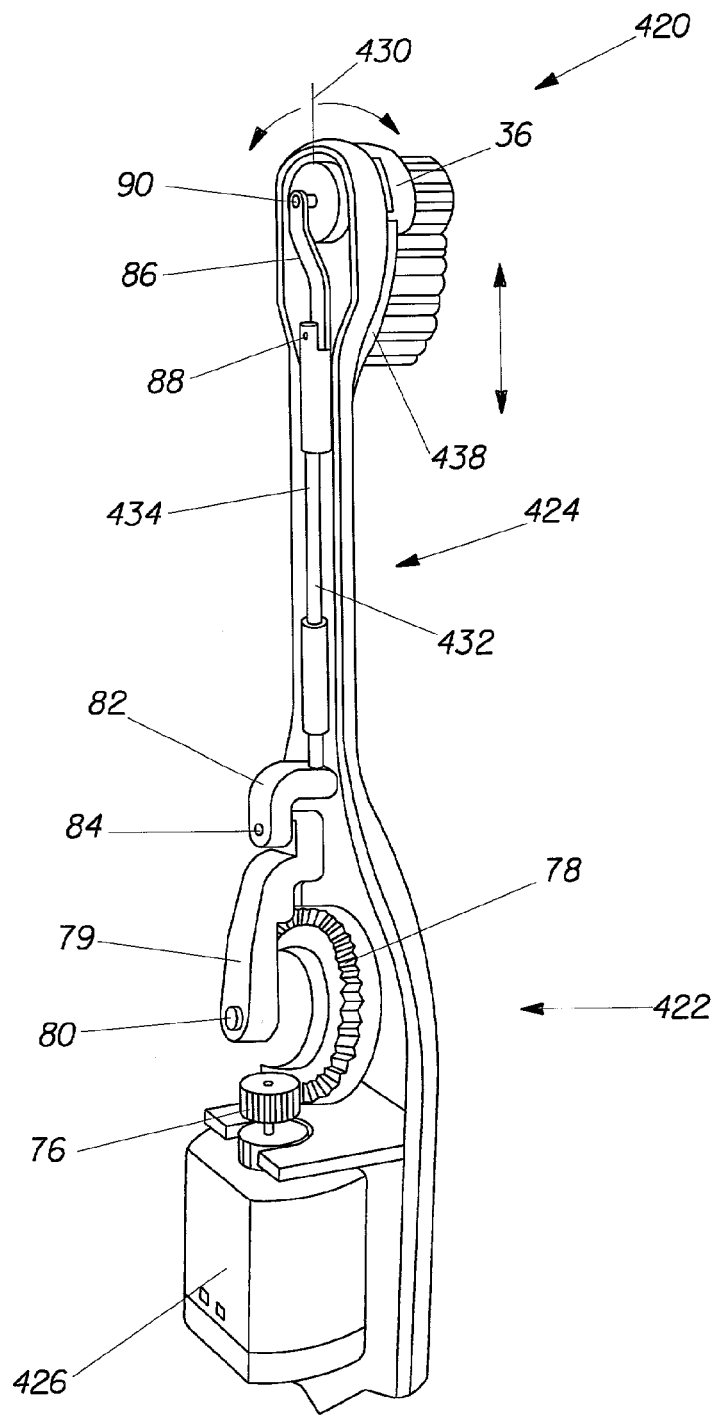
FIG. 9 is a perspective view of an electric toothbrush made in accordance with the present invention, wherein part of the toothbrush housing has been removed in order to illustrate otherwise hidden features and wherein the electric toothbrush incorporates a shaft which reciprocates.

Turning to FIG. 9, the electric toothbrush comprises a toothbrush head 420, a body or handle 422, and an elongate neck 424 there between. The drive train, which consists of the shafts and gears that transmit motion from the motor to the first bristle holder 36, is similar to that describe in U.S. Pat. No. 6,178,579, the substance of which is incorporated herein by reference. The handle 422 is hollow and includes a motor 426 and batteries (not shown) for powering the motor. A rechargeable power source can be substituted for the batteries. The head 420 has a longitudinal axis 430 passing there through. The longitudinal axis 430 extends in the same general longitudinal direction as a longitudinal axis 432 of a shaft 434. A first bristle holder 36 is disposed at a first end of the head 420, wherein the first end is at the forward most point of the head 420. While the first bristle holder 36 is illustrated as circular in shape, other shapes can be utilized. Further, while the first bristle holder 36 is disposed at the first end of the head 20, it will be appreciated that it can be disposed away from the first end and other features, such as stationary bristles, might be disposed between the first bristle holder 36 and the first end of the head 20. In this embodiment, the first bristle holder only oscillates and does not reciprocate, translate, or perform any other non-rotational or oscillatory motion.

A second bristle holder 438 is disposed adjacent the first bristle holder 436. The second bristle holder reciprocates in the same general longitudinal direction as longitudinal axis 430 of the head 420. In this embodiment, the longitudinal direction of reciprocation is also the same as the longitudinal direction of the longitudinal axis 432 of the shaft 434. While it is desirable to locate the second bristle holder 438 directly adjacent the first bristle holder 36, it is contemplated that a gap may be provided between the first and second bristle holders. In addition, the gap between the first and second bristle holders might be filled with stationary bristles which are embedded in fixed or stationary third bristle holder (not shown) which forms part of the toothbrush head.

A first gear 76 is operatively connected to and powered by the motor 426. A second gear 78 is operatively connected to the first gear 76. The rotational axis of the second gear 78 is approximately normal to the rotational axis of the first gear 76 such that the teeth of the first gear 76 mesh with teeth of the second gear 78, thus causing second gear 78 to rotate as the first gear 76 rotates.

A first arm 79 is eccentrically and pivotably connected to the second gear 78 via a pin 80 or other fastening device. Due to the eccentric connection, the rotational motion of the second gear 78 is converted into a reciprocating motion of the first arm 79. A second arm 82 is pivotably connected to the first arm 79 via a pin 84 or other fastening device. The shaft 434 is fixedly secured, such as by a press fit, to the second arm 82 and to a third arm 86 by a pin 88. The shaft 434 is housed at least partially within the neck 424. The third arm 86 is connected at its terminal end to the first bristle holder 36 via a pin 90 or other fastening device. The terminal end of the third arm 86 is offset from the longitudinal axis of the shaft 434 so that it is pinned adjacent the outer periphery of the first bristle holder 36. This offset arrangement converts the reciprocating motion of the third arm 86 into an oscillating motion of the first bristle holder 36, wherein the first bristle holder 36 oscillates about an axis approximately normal to the axis 432 of the shaft 434.

Figure 10:
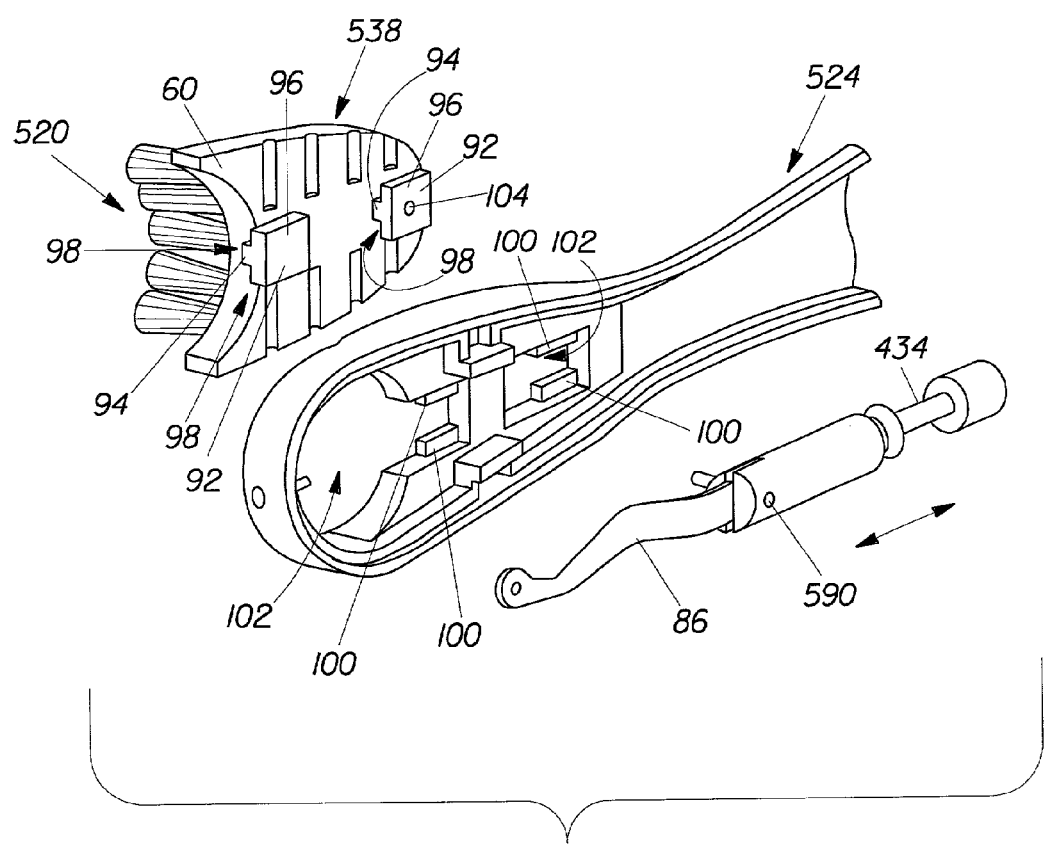
FIG. 10 is an exploded perspective view of a first embodiment of a toothbrush head suitable for use with the electric toothbrush of FIG. 9.

Referring to FIG. 10, a first embodiment of a toothbrush head suitable for use with the electric toothbrush of FIG. 9 will now be described. In the head 520, the pin 590 that interconnects the shaft 434 with the third arm 86 also extends into the second bristle holder 538. The second bristle holder 538 is thereby driven in the same general longitudinal direction as the longitudinal axis of the head 520 and/or the shaft 434. A plurality of T-shaped (in cross section) blocks 92 depend from a bottom surface 60 of the second bristle holder 538. The T-shaped blocks 92 are formed by an upstanding portion 94 which is connected to a transverse portion 96. Slots 98 are formed between the bottom surface 60 of the second bristle holder 538, a side wall of the upstanding portion 94, and an inner side wall of the transverse portion 96. The slots 98 extend in the same general longitudinal direction as the longitudinal axis of head 520. Two pairs of protrusions 100 extend from two cut-outs 102 in the housing. The cut-outs 102 receive the T-shaped blocks 92. One of the cut-outs 102 also has a circular portion which receives the circular shaped first bristle holder (not shown in FIG. 10). The protrusions 100 are slideably received within the slots 98 of the T-shaped blocks 92 when the second bristle holder 538 is installed in the top housing of the head 520. The protrusions 100 and slots 98 cooperate to direct the motion of the second bristle holder 538 in the same general longitudinal direction as the longitudinal axis of the head 520 and/or shaft 534 during use. The rearward most T-shaped block (i.e., the T-shaped block located adjacent the neck) has a hole 104 which receives the pin 590.

As the shaft 434 reciprocates, the pin 590 also reciprocates thereby driving the rearward T-shaped block 92 having the hole 104, and therefore the second bristle holder 538, in a reciprocating longitudinal motion. In addition, the shaft 434 drives the third arm 86 in a reciprocating motion which in turn drives first bristle holder 36 in an oscillating motion, as previously described. In one embodiment, the first bristle holder 36 moves in counter-clockwise direction as the second bristle holder 538 moves away from the handle 422 in a direction toward the first bristle holder 36.

Figure 11:
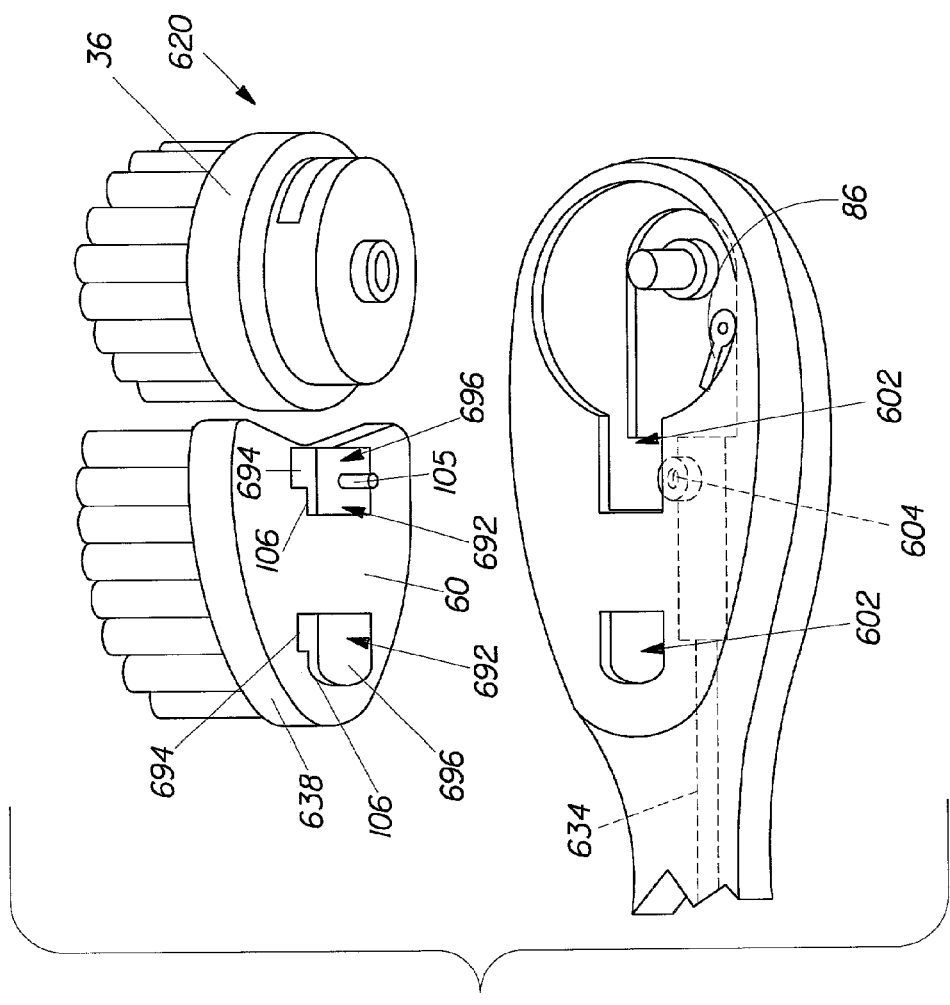
FIG. 11 is an exploded perspective view of a second embodiment of a toothbrush head suitable for use with the electric toothbrush of FIG. 9.

Referring to FIG. 11, a second embodiment of a toothbrush head suitable for use with the electric toothbrush of FIG. 9 will now be described. In the head 620, a second bristle holder 638 is disposed adjacent a first bristle holder 36. The second bristle holder 638 has first and second L-shaped (when viewed from the side) blocks 692 that depend from a bottom surface 60 of the second bristle holder 638. While L-shaped blocks are shown, other shapes can be substituted. The L-shaped blocks 638 are formed from an upstanding portion 694 and a longitudinally-directed portion 696 that is aligned in the same direction as the longitudinal axis of the head 620 and/or shaft 634. The L-shaped blocks 692 are received within corresponding slots 602 such that the side walls of the L-shaped blocks 692 and the side walls of the slots 602 cooperate to direct the reciprocating motion of the second bristle holder 638. The underside of a cantilevered portion 106 of the longitudinal portion 696 of the L-shaped blocks 638 engages an inner surface of the toothbrush head housing to retain the second bristle holder 638 with the head 620. The second bristle holder 638 includes a pin 105 which extends from the forward most L-shaped block 692. The pin 105 may be molded and unitary with the L-shaped block 692. The pin 105 is received in a hole 604 associated with the shaft 634 at about the point where the shaft 634 and the third arm 86 are connected. As the shaft 634 reciprocates in the same general direction as the longitudinal axis of the head 620, the pin 105 also reciprocates in generally the same direction, thereby reciprocating the second bristle holder 638 in the same general longitudinal direction as the longitudinal axis of the head 620 and/or shaft 634. The side walls of the slots 602 slidingly engage the side walls of the L-shaped blocks 692, thereby preventing the second bristle holder 638 from moving significantly in a transverse direction. The third arm 86 also drives the first bristle holder 36 in an oscillatory motion as previously discussed with respect earlier embodiments of the present invention.

Figure 12:
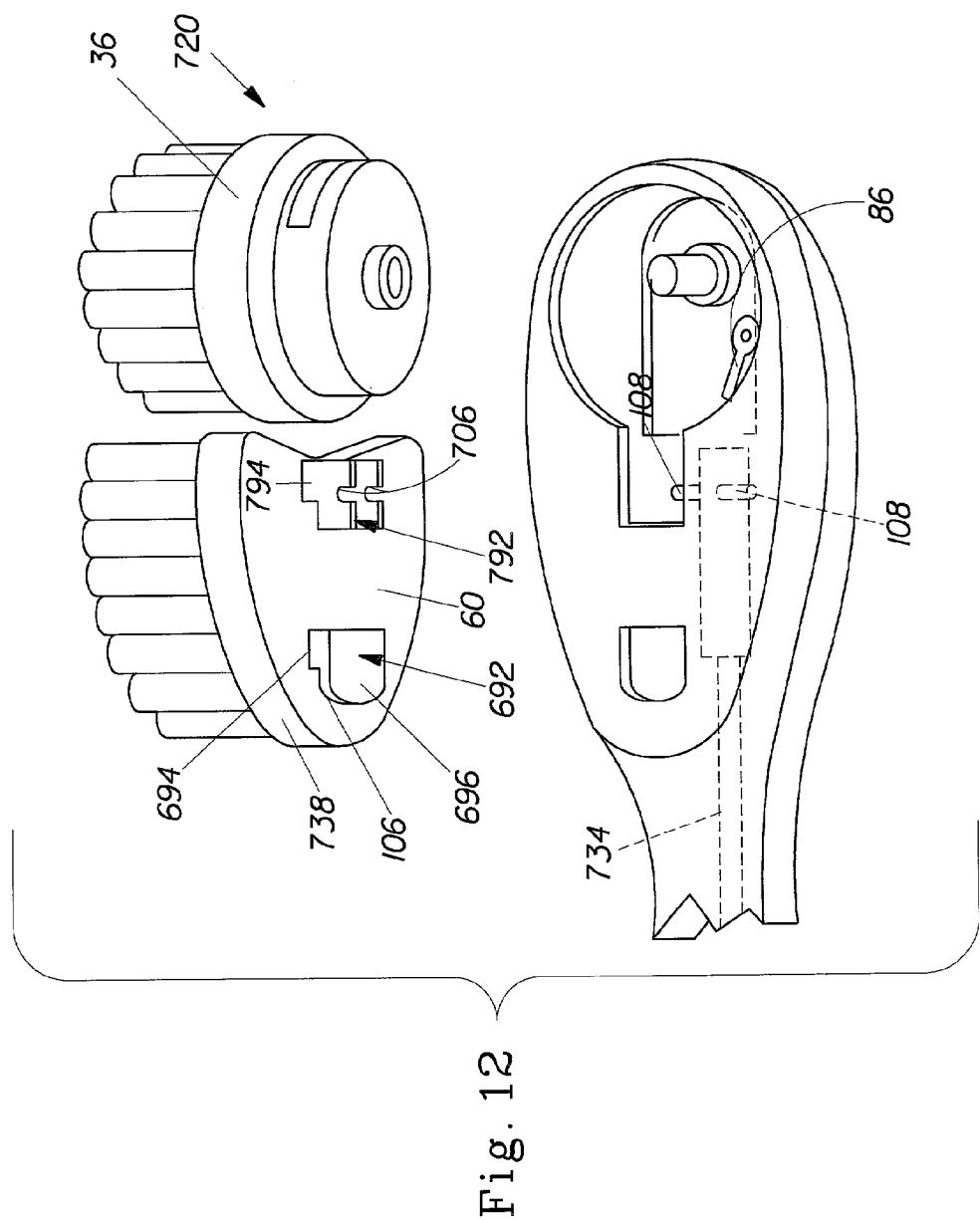
FIG. 12 is an exploded perspective view of a third embodiment of a toothbrush head suitable for use with the electric toothbrush of FIG. 9.

Referring to FIG. 12, a third embodiment of a toothbrush head suitable for use with the electric toothbrush of FIG. 9 will now be described. In the head 720, a second bristle holder 738 is disposed adjacent a first bristle holder 36. The second bristle holder 738 has two L-shaped (in side view) blocks 692 and 792 disposed at the forward and rearward edges of the second bristle holder 738. However T, I or other shaped blocks could also be used. The blocks 692, 792 extend from a bottom surface 60 of the second bristle holder 738. The L-shaped block 692 is the same as previously described for FIG. 11. The L-shaped block 792 has a pair of opposed upstanding portions 794 which each contain a U-shaped slot 706. The U-shaped slots 706 each receive a corresponding pin 108 which extends transversely from the shaft 734. As the shaft 734 reciprocates in the same longitudinal direction as the longitudinal axis of the head 720, the pins 108 also reciprocate, thereby driving the L-shaped blocks 692, 792 and the second bristle holder 738 in the same manner. The third arm 86, which is connected to the shaft 734, drives the first bristle holder 36 in an oscillatory motion as previously.

Figure 13:
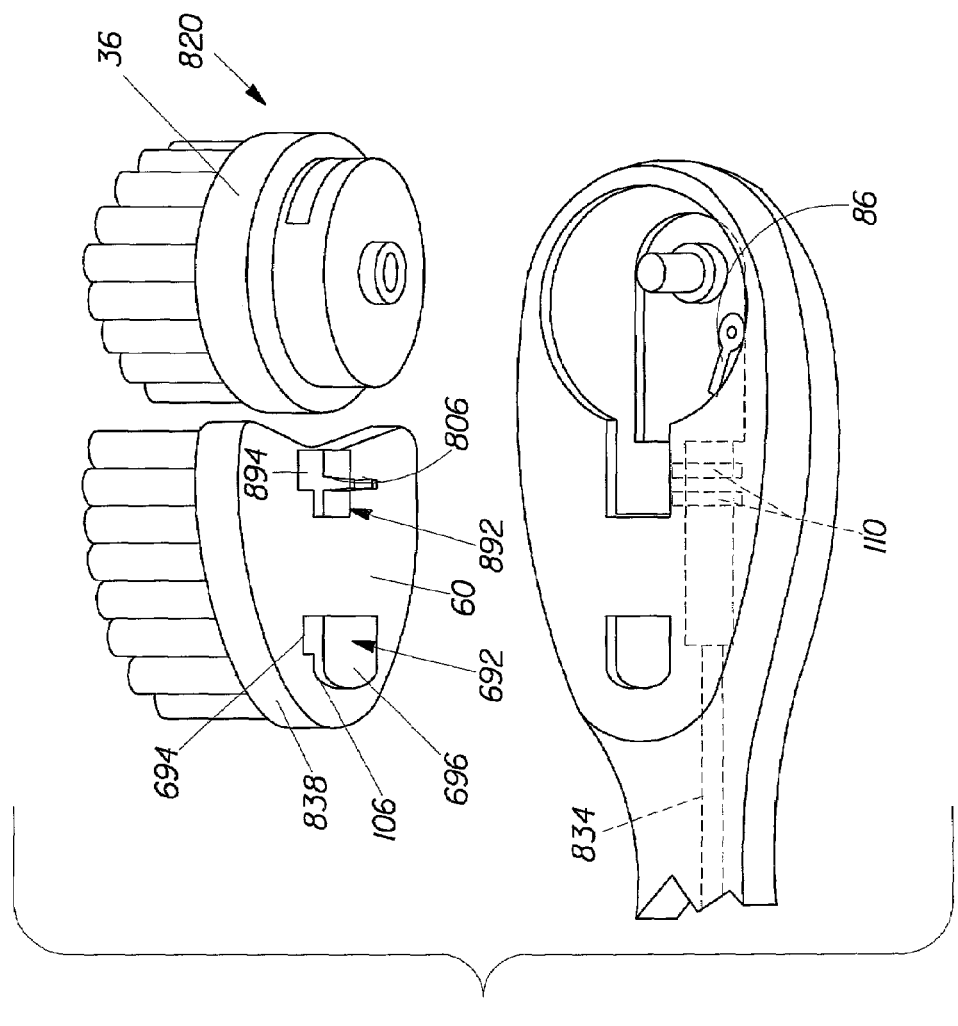
FIG. 13 is an exploded perspective view of a fourth embodiment of a toothbrush head suitable for use with the electric toothbrush of FIG. 9.
Figure 14:
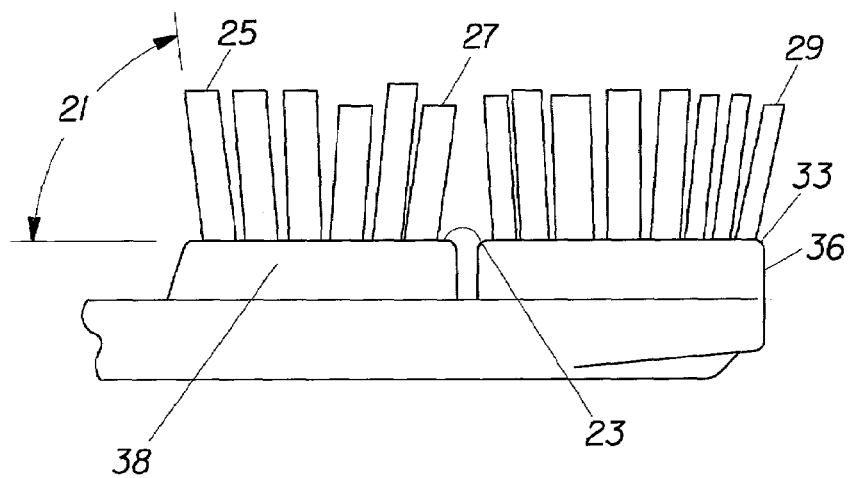
FIG. 14 is a side elevational view of a toothbrush bristle tuft pattern suitable for use with the electric toothbrushes of FIGS. 1 and 9, wherein some of the bristle tufts form an acute angle with the top surface of the bristle holders.
Figure 15:
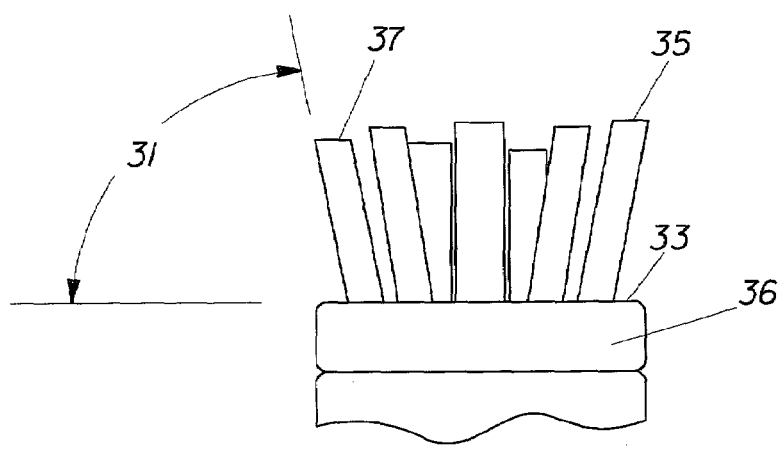
FIG. 15 is a front elevational view of the toothbrush head of FIG. 16.

Referring to FIG. 13, a fourth embodiment of a toothbrush head suitable for use with electric toothbrush of FIG. 9 will now be described. In the head 820, a second bristle holder 838 is disposed adjacent a first bristle holder 36. The second bristle holder 838 has two L-shaped (in side view) blocks 692 and 892 disposed at the forward and rearward edges of the second bristle holder 838. However T, I or other shaped blocks could also be used. The blocks 692, 892 extend from a bottom surface 60 of the second bristle holder 838. The L-shaped block 692 is the same as previously described for FIG. 11. The L-shaped block 892 has an upstanding portion 894 with a C-shaped slot 806 that is sized to slideably receive the shaft 834. A pair of spaced apart rings 110 circumscribe the shaft 834. When assembled, the shaft 834 is received in the C-shaped slot 806 such that the upstanding portion 894 is disposed between the rings 110. As the shaft 834 reciprocates in the same general direction as the longitudinal axis of the head 820, the rings reciprocate the L-shaped block 892 and therefore also the second bristle holder 838 in the same manner. The third arm 86 also drives the first bristle holder 36 in an oscillatory motion as previously discussed. While embodiments of the present invention have been illustrated for simplicity with tufts of bristles that extend in a direction substantially perpendicular to the top surface of the bristle holders, it is contemplated that the bristles might be arranged differently to complement or further enhance the motions of the first and/or second bristle holders. Referring to FIGS. 14 and 15, some or all of the bristles might extend in a direction which forms an acute angle 21 with the top surfaces 23, 33 of the first and second bristle holders 36, 38 and extends in a forward or rearward direction, such as shown by way of example with respect to bristle tufts 25, 27, and 29 respectively. Referring to FIG. 15, in another embodiment, some of the bristles might extend outwardly away from head, in another direction, again forming an acute angle 31 with respect to the top surface 23, 33 of the first and second bristle holders 33, 38, as shown by way of example with respect to bristle tufts 35 and 37. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910; the substances of which are incorporated herein by reference.

Figure 16:
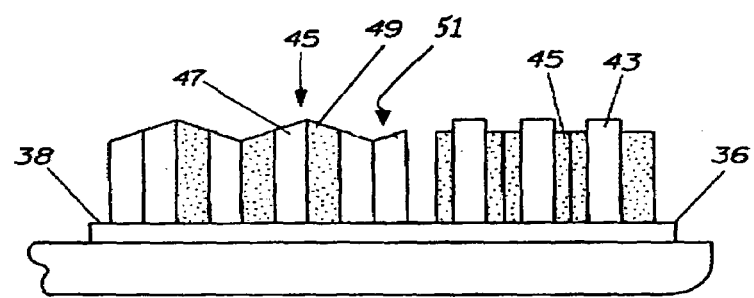
FIG. 16 is a side elevational view of toothbrush bristle tuft pattern suitable for use with the electric toothbrushes of FIGS. 1 and 9.
Figure 17:
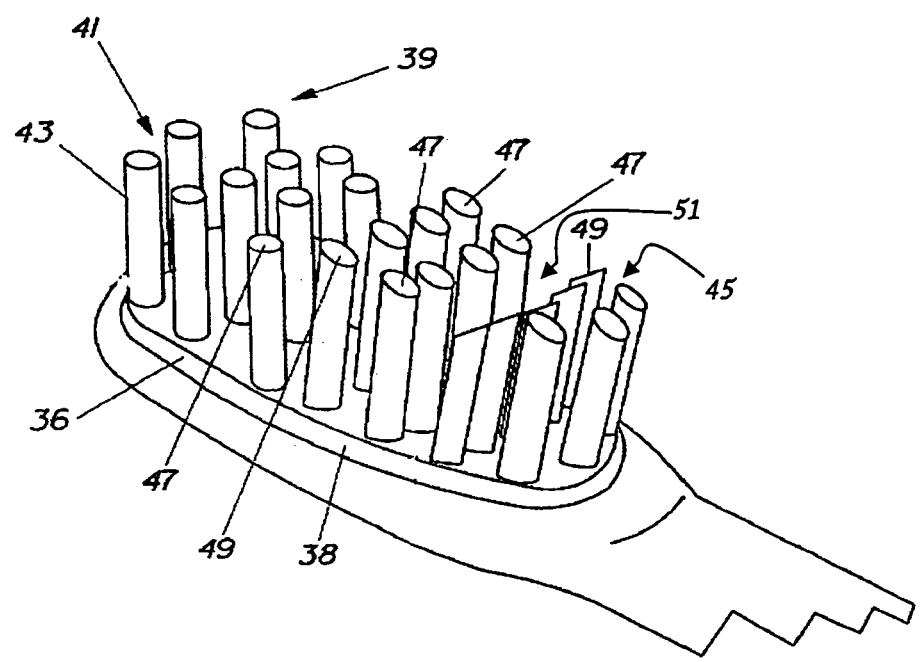
FIG. 17 is a perspective view of the toothbrush head of FIG. 16.
Figure 18:
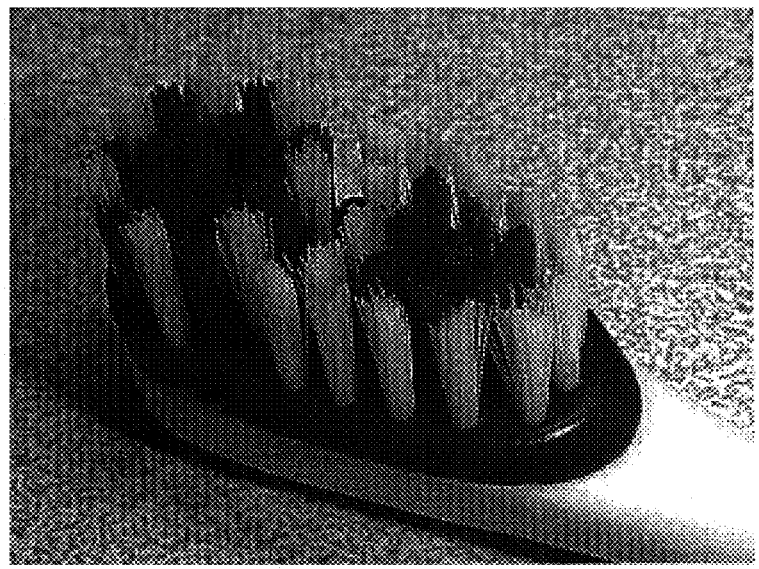
FIG. 18 is a photographic perspective view of the toothbrush head of FIG. 16.
Figure 19:
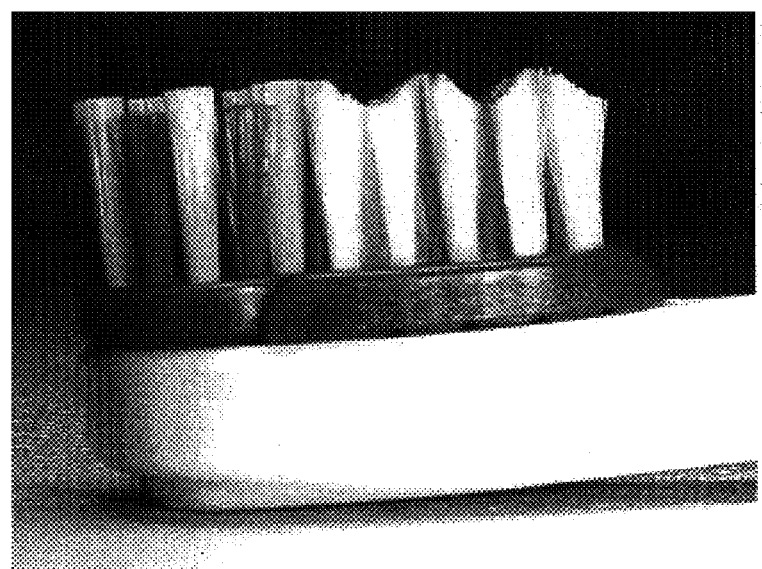
FIG. 19 is a photographic side elevational view of the toothbrush head of FIG. 18.
Figure 20:
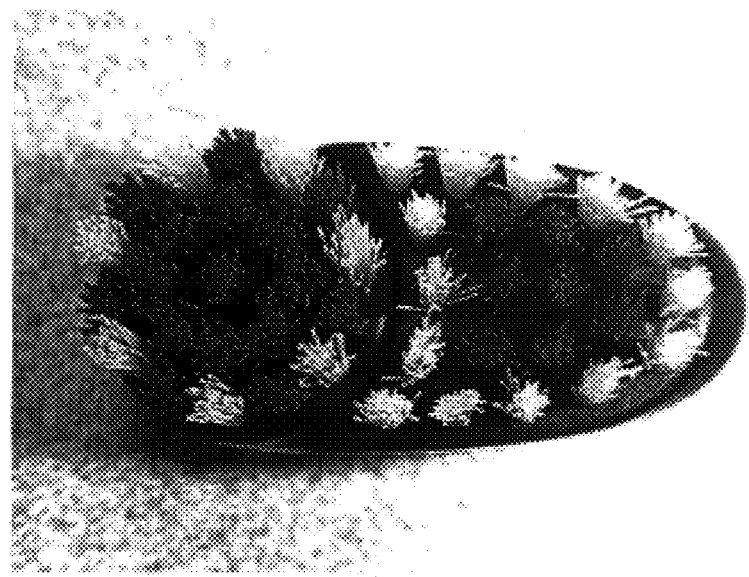
FIG. 20 is a photographic top planar view of the toothbrush head of FIG. 18.
Figure 21:
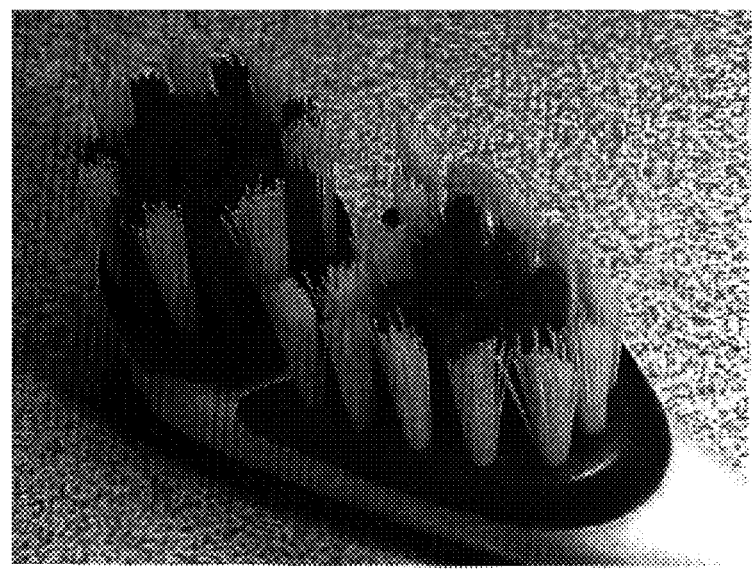
FIG. 21 is a photographic perspective view of a toothbrush head having the bristle pattern of FIG. 16, wherein the second bristle holder is shown in a second position.
Figure 22:
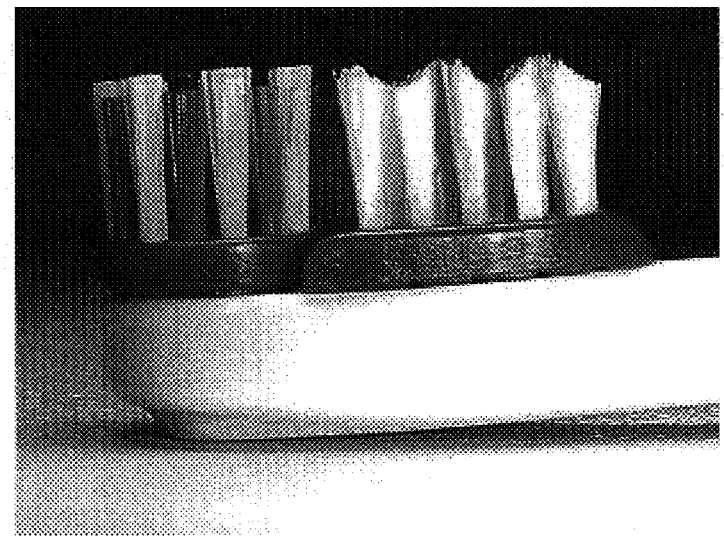
FIG. 22 is a photographic side elevational view of the toothbrush head of FIG. 21.
Figure 23:
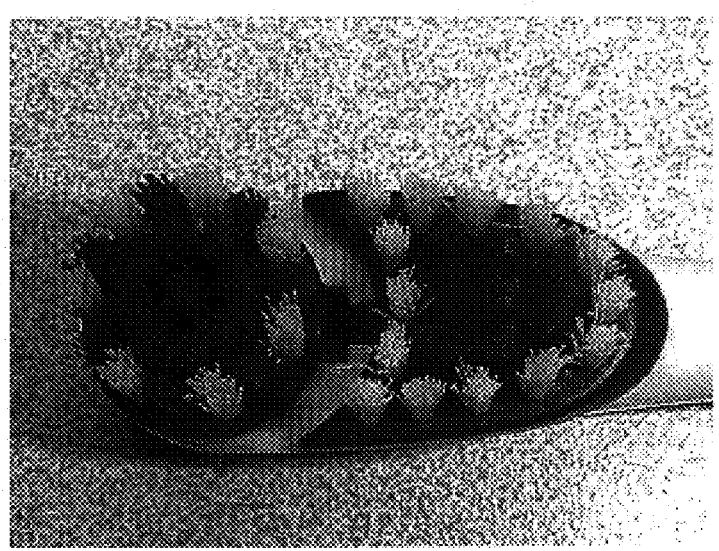
FIG. 23 is a photographic top planar view of the toothbrush head of FIG. 21.
Figure 24:
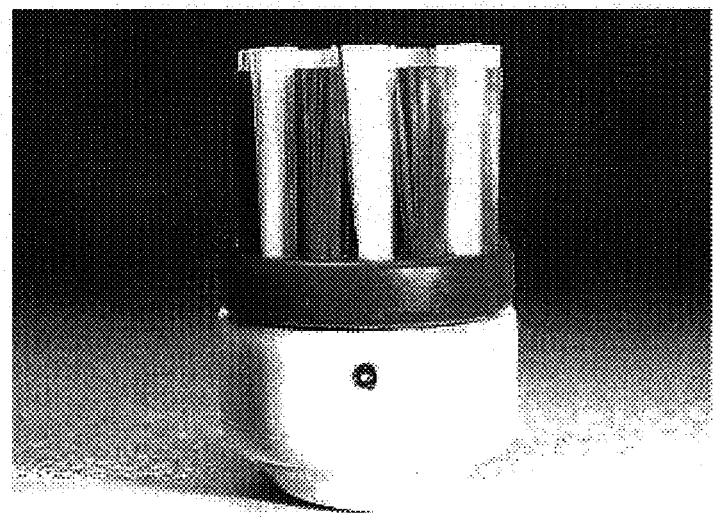
FIG. 24 is a photographic front elevational view of the toothbrush head of FIGS. 18 and 21.
Figure 25:
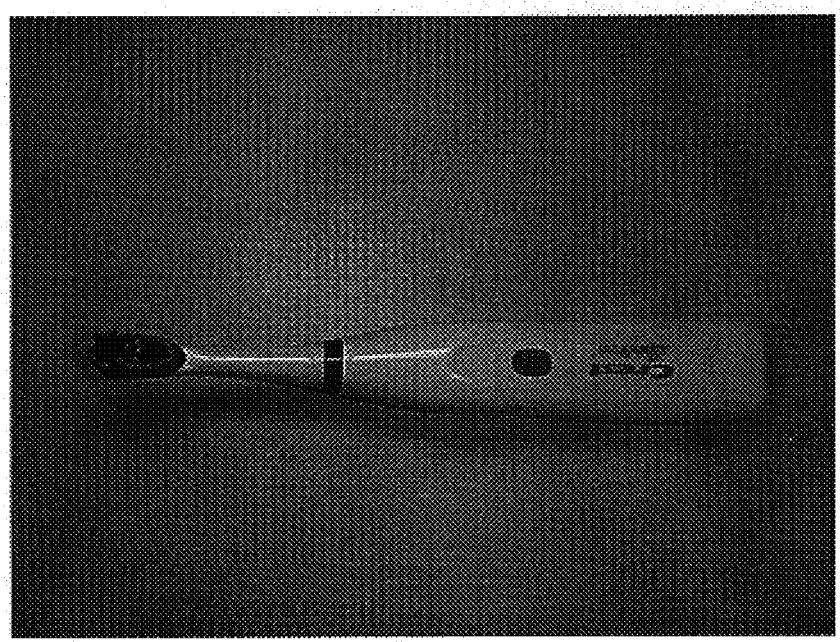
FIG. 25 is a photographic top planar view of the toothbrush head of FIG. 18 in combination with a handle.
Figure 26:
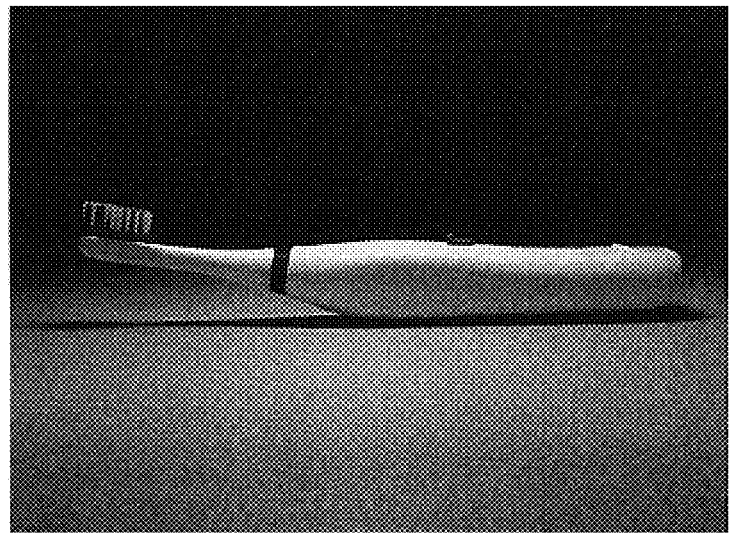
FIG. 26 is a photographic side view of the toothbrush of FIG. 25.
Figure 27:
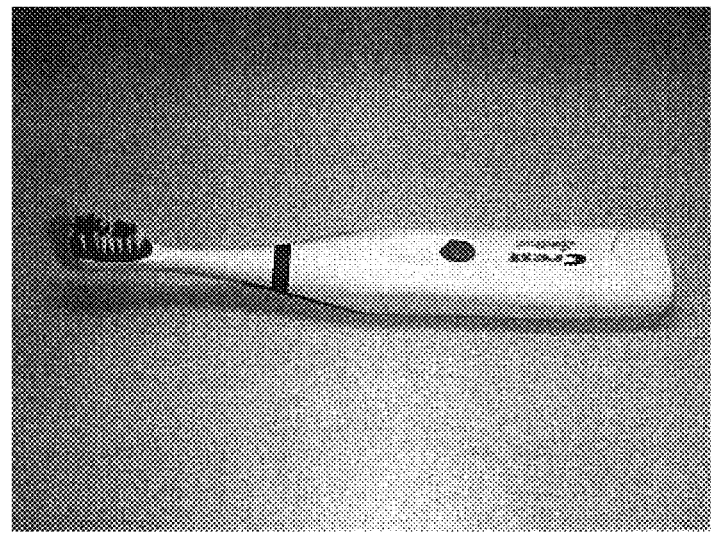
FIG. 27 is a photographic perspective view of the toothbrush of FIG. 25.

While the electric toothbrushes of the present invention can be made with any combination of bristle or massaging tip types, dimensions, combinations, angles and arrangements, a particularly preferred arrangement is illustrated in FIGS. 16 and 17. The first bristle holder 36 has two concentric rings of tufts, wherein the outer ring 39 has between 10 and 20 tufts and the inner ring 41 has between 6 and 10 tufts. In one embodiment, the outer ring 39 has 14 tufts and the inner ring 41 has 8 tufts. Between 1 and 2 tufts are disposed inside the inner ring 39 at the center of the first bristle holder. Tufts in the outer ring 39 alternate in height. In one embodiment there are seven tall tufts 43 and seven shorter tufts 45. The difference in length between the tall tufts 43 and the shorter tufts 45 is between about 0.5 mm and about 2.5 mm in one embodiment and between about 1 mm and about 2 mm in other embodiment. The tall and short tufts of bristles can be provided with different characteristics. For example, the tall tufts of bristles may be relatively soft for gently cleaning and massaging gums of a user while shorter tufts of bristles may be somewhat firmer for interdental cleaning (or vice versa). This arrangement allows the longer (and typically softer bristles) to be pressed, bent and deflected against the gums of the user before the shorter (and typically firmer bristles) contact the teeth and gums of the user. Therefore, for example, soft bristles can be applied with more force while stiffer (and perhaps less comfortable bristles) are applied with less force.

The first bristle holder 36 oscillates (i.e., the angle of rotation) between about 20 degrees and about 45 degrees in one embodiment and between about 25 degrees and about 35 degrees in another embodiment. The first bristle holder has a peak oscillation frequency between about 6,000 and about 10,000 cycles per minute in one embodiment and between about 7,000 and 9,000 cycles per minute in another embodiment. A cycle is one complete clockwise and counter-clockwise rotation (or vice versa) when the batteries are fully charged. It is contemplated that the oscillation frequency may drop outside of these ranges as the batteries are drained by use. Since the same shaft is driving both the first and second bristle holders, the second bristle holder would also have the same frequency of operation. A cycle for the second bristle holder is one complete stroke toward the handle and one complete stroke back toward the first bristle holder (or vice versa).

The second bristle holder 38 has between 15 and 40 tufts in one embodiment and between about 20 and about 30 tufts in another. The tufts are arranged in between about 5 and about 15 rows, as best seen in FIG. 16. The rows may be linear or curvilinear. The tips of the tufts of bristles are provided with a linear, wave-like profile when viewed from the side, as best seen in FIG. 16, although this profile can be more curvilinear. This arrangement has between 2 and about 8 peaks 45 in one embodiment and between about 3 and about 6 peaks 45 in another embodiment, when viewed from the side. The peaks 45 are formed by adjacent tufts that have oppositely angled tuft end surfaces 47 and 49. The same is true for the valleys 51. The distance from peak-to-peak is between about 2 mm and about 10 mm in one embodiment and between about 4 mm and about 6 mm in another embodiment. The depth from peak-to-valley is between about 0.5 mm and about 3 mm in one embodiment and between about 1 mm and about 2 mm in another embodiment. Each tuft is cut at about 45 degrees. The tuft arrangement of the second bristle holder 38 has a length between about 5 mm and about 20 mm and a width between about 5 mm and 15 mm in one embodiment and a length between about 10 mm and about 15 mm and a width between about 10 mm and 15 mm in another embodiment. The tuft pattern of the second bristle holder 38 tapers toward the longitudinal axis of the toothbrush head as the taper progresses rearward. The second bristle holder has a stroke (i.e., a displacement in one direction) between about 1 mm and about 6 mm in one embodiment and a stroke between about 2 mm and about 4 mm in another embodiment. The wave-like tuft profile of the second bristle holder 38 can also be used in an electric toothbrush embodiment where the second bristle holder 38 does not move, such as with the electric toothbrush described in U.S. Pat. No. 6,630,395.

The invention has been described with reference to particular embodiments. Modifications and alterations will occur to others upon reading and understanding this specification. For example, while certain cams have been described as comprising bends in a shaft and other cams have been described as including appropriately shaped beads secured to a shaft, the cams are not limited to the suggested form. Indeed, bends may be substituted for beads and beads may be substituted for bends and other shapes, sizes, and configurations can be implemented. It is intended that all such modifications and alterations are included insofar as they come within the scope of the appended claims or equivalents thereof.

What is claimed is:

1. An electric toothbrush, comprising:
a handle having a motor disposed therein;
a drive system operatively connected to said motor, said drive system comprising
a shaft with a longitudinal axis and configured to reciprocate along its longitudinal axis and an arm extending from an end of the shaft in generally the same direction as the longitudinal axis of said shaft;
a head having a longitudinal axis which extends in generally the same direction as the longitudinal axis of said shaft;
a neck disposed between said handle and said head;
a first bristle holder operatively connected to said arm to oscillate or rotate; and
a second bristle holder operatively connected to said shaft to reciprocate in generally the same direction as said longitudinal axis of said head but not to rotate or oscillate; and
wherein said second bristle holder comprises a row of bristle tufts oriented generally transverse to said longitudinal axis of said head.

2. The electric toothbrush of claim 1, wherein said second bristle holder is disposed between said first bristle holder and said handle.

3. The electric toothbrush of claim 2, wherein said first bristle holder and said second bristle holder do not physically contact each other.

4. The electric toothbrush of claim 3, wherein said shaft is coupled to said second bristle holder, and wherein said arm is coupled to said first bristle holder.

5. The electric toothbrush of claim 2, wherein said transverse row is arcuate, and wherein said first bristle holder is generally circular, such that said transverse row partially wraps around said first bristle holder.

6. The electric toothbrush of claim 1, wherein said shaft comprises a pin, wherein said pin operatively connects said shaft and said second bristle holder.

7. The electric toothbrush of claim 1, wherein a bottom surface of said second bristle holder contacts a top surface of said head.

8. The electric toothbrush of claim 7, wherein said head defines an aperture and said second bristle holder comprises a depending element which depends from said bottom surface of said second bristle holder, and wherein said depending element is received through said aperture of said head.

9. An electric toothbrush comprising:
a handle having a motor disposed therein:
a drive system operatively connected to said motor, said drive system comprising
a shaft with a longitudinal axis, wherein said shaft reciprocates;
a head having a longitudinal axis;

a neck disposed between said handle and said head;

a first bristle holder associated with said head which oscillates or rotates;

a second bristle holder associated with said head which reciprocates in generally the same direction as said longitudinal axis of said head but does not rotate or oscillate, wherein said second bristle holder further comprises a first T-shaped block which depends from a bottom surface of said second bristle holder, wherein said T-shaped block slideably engages a first pair of projections of said head to guide the movement of said second bristle holder, wherein said drive system is operatively connected to said first and second bristle holders; and wherein said second bristle holder comprises a row of bristle tufts oriented generally transverse to said longitudinal axis of said head.

10. A detachable head for use with an electric toothbrush, said detachable head comprising:

an elongate body comprising a drive system with a shaft with a longitudinal axis and an arm extending from an end of the shaft in generally the same direction as the longitudinal axis of the shaft, a head having a longitudinal axis which extends in generally the same direction as the longitudinal axis of said shaft, and a first end opposite a second end, wherein said first end may be detachably coupled to the electric toothbrush, said shaft configured to reciprocate along its longitudinal axis;

a first bristle holder comprising a first plurality of bristle tufts, wherein said first bristle holder is operatively connected to said arm of said drive system to oscillate said first bristle holder about an axis substantially perpendicular to said longitudinal axis of said head;

a second bristle holder comprising a second plurality of bristle tufts, wherein said second bristle holder is operatively connected to said shaft of said drive system to reciprocate said second bristle holder in generally the same direction as said longitudinal axis of said head, wherein said second bristle holder does not rotate or oscillate;

wherein a bottom surface of said second bristle holder contacts a top surface of said head; and wherein said head comprises an aperture and said second bristle holder comprises a depending element which depends from said bottom surface of said second bristle holder, and wherein said depending element is received through said aperture of said head.

11. The detachable head of claim 10, wherein a bottom surface of said first bristle holder contacts said top surface of said head.

12. The detachable head of claim 10, wherein said second bristle holder comprises a row of bristle tufts generally transverse to said longitudinal axis of said head.

13. The detachable head of claim 12, wherein said generally transverse row is arcuate, and wherein said first bristle holder is generally circular, such that said generally transverse row partially wraps around said first bristle holder.

14. The detachable head of claim 13, wherein said second bristle holder is disposed between said first bristle holder and said first end.

15. The detachable head of claim 13, wherein said first bristle holder and said second bristle holder do not physically contact other.

16. The detachable head of claim 10, wherein said shaft is coupled to said second bristle holder and said arm is coupled to said first bristle holder.

17. A detachable head for use with an electric toothbrush, said detachable head comprising:

an elongate body comprising a head, a drive system, and a first end opposite a second end, wherein said first end may be detachably coupled to the electric toothbrush, said head having a longitudinal axis;

a first bristle holder comprising a first plurality of bristle tufts, wherein said first bristle holder is operatively connected to said drive system to oscillate said first bristle holder about an axis substantially perpendicular to said longitudinal axis;

a second bristle holder comprising a second plurality of bristle tufts, wherein said second bristle holder is operatively connected to said drive system to reciprocate said second bristle holder in generally the same direction as said longitudinal axis of said head, wherein said second bristle holder does not rotate or oscillate; and said drive system comprising a shaft configured to reciprocate along a longitudinal axis in generally the same direction at the longitudinal axis of said head and an arm extending from an end of the shaft, wherein said arm generally extends in the direction of said longitudinal axis of said head, and wherein said shaft is coupled to said second bristle holder and said arm is coupled to said first bristle holder.

18. The detachable head of claim 17, wherein a bottom surface of said first bristle holder and a bottom surface of said second bristle holder contact a top surface of said head, and wherein said head comprises an aperture and said second bristle holder comprises a depending element which depends from said bottom surface of said second bristle holder, and wherein said depending element is received through said aperture of said head.

19. The detachable head of claim 18, wherein said second bristle holder comprises a row of bristle tufts generally transverse to said longitudinal axis of said head.

20. The detachable head of claim 19, wherein said generally transverse row is arcuate, and wherein said first bristle holder is generally circular, such that said generally transverse row partially wraps around said first bristle holder, and wherein said second bristle holder is disposed between said first bristle holder and said first end.

* * * * *